United States Patent
Grover et al.

(10) Patent No.: US 8,084,060 B2
(45) Date of Patent: Dec. 27, 2011

(54) FIBROUS CALCIUM PYROPHOSPHATE PARTICLES AND METHODS OF MAKING AND USING SAME

(75) Inventors: Liam M. Grover, Bewdley (GB); Jake E. Barralet, Montreal (CA)

(73) Assignee: Nanunanu Ltd., Bristol (GB)

( * ) Notice: Subject to any disclaimer, the term of this patent is extended or adjusted under 35 U.S.C. 154(b) by 42 days.

(21) Appl. No.: 12/373,198

(22) PCT Filed: Jul. 11, 2007

(86) PCT No.: PCT/CA2007/001221
§ 371 (c)(1),
(2), (4) Date: Apr. 16, 2009

(87) PCT Pub. No.: WO2008/006204
PCT Pub. Date: Jan. 17, 2008

(65) Prior Publication Data
US 2009/0291930 A1    Nov. 26, 2009

Related U.S. Application Data

(60) Provisional application No. 60/830,252, filed on Jul. 12, 2006.

(51) Int. Cl.
*A61K 9/14* (2006.01)
(52) U.S. Cl. ........................................ 424/489
(58) Field of Classification Search ............ None
See application file for complete search history.

(56) References Cited

U.S. PATENT DOCUMENTS
5,676,917 A    10/1997 Trudeau et al.

FOREIGN PATENT DOCUMENTS
WO    WO 02/41844 A2    5/2002

OTHER PUBLICATIONS

Ishikawa et al. J of Bone and Joint Surgery, 1989, vol. 71, pp. 875-886.*
O. Masala et al., Modeling the formation of granules: the influence of manganese ions on calcium pyrophosphate precipitates, Inorganica Chimica Acta, 2002, vol. 339, pp. 366-372.
Liu, et al. "Creating New Supramolecular Materials by Architecture of Three-Dimensional Nanocrystal Fiber Networks," J. Am. Chem Soc. 2002, 124, 15055-15063.
Shinozaki et al., "Calcium Pyrophosphate Dihydrate (CPPD) Crystal Dissolution by Alkaline-Phosphatase-Interaction of Alkaline-Phosphatase on Cppd Crystals," J. of Rheumatology, 22(1) 117 (1995).
Remington: the Science and Practice of Pharmacy, 19th edition, Mack Publishing Co., Easton PA (1995).
Masala et al., "Formation of Spherical Granules of Calcium Pyrophosphate," Crystal Growth and Design, vol. 3, 431 (2003).

* cited by examiner

*Primary Examiner* — Suzanne M. Noakes
(74) *Attorney, Agent, or Firm* — Dowell & Dowell, P.C.

(57) ABSTRACT

Fibrous calcium pyrophosphate particles with a unique fibrous nanostructure are disclosed. The invention includes a composition, comprising fibrous particles, wherein the fibrous particles include fibers and the fibers include calcium and pyrophosphate. Also included are methods for making calcium pyrophosphate particles wherein solutions of calcium salt and pyrophosphate salt are combined to form the particles. Pharmaceutical compositions and methods for treating a patent using the disclosed particles are also described.

22 Claims, 18 Drawing Sheets

FIBROUS CALCIUM PYROPHOSPHATE PARTICLES AND METHODS OF MAKING AND USING SAME

RELATED APPLICATION

This application claims the benefit of U.S. Provisional Patent Application No. 60/830,252, filed on Jul. 12, 2006, the entire teachings of which are incorporated herein by reference.

BACKGROUND OF THE INVENTION

It may be desirable to load a therapeutic compound onto or within particles of biomaterial for one or more of three main reasons: to carry, to store, or to sustain release. Drug carriers may have a specific function such as, for example, preventing degradation in the gut or to transport the molecules to a target organ or tissue. Storage in or on particles can occur by simple surface adsorption and can be limited by the specific surface area of the material. Alternatively, particles can be formed into porous agglomerates by gelation or sintering and the drug can be absorbed into the pore volume. Controlled release may occur by altering the binding affinity of the drug with the surface to control desorption, or a polymer layer or tortuosity provided by nanoporosity can act as a diffusion barrier or release may be mediated by dissolution of the ceramic particles themselves. Precipitation of inorganic bioceramic materials normally results in macro or microscale crystals with a correspondingly low specific surface area. A need exists for novel sustained release formulations.

There is considerable interest in the development of new materials that are capable of delivering a consistent and effective dose of therapeutic drugs and proteins in vivo. Problems with currently available materials include the requirement of a high-temperature processing step, which can damage heat sensitive molecules and a so called "burst-release" of the therapeutic agent following administration. Many different materials have been investigated for use as drug delivery matrices. However, choice of materials on offer to the biomaterials scientist is limited since any material that is used must be non-cytotoxic. One approach to the design of new biomaterials devices is to control the steps involved in the manufacturing process of already used materials to produce novel structures with improved efficiency in their given applications. Liu et al. attempted to form nanofiber networks which are capable of entrapping drugs and proteins in their meshes and consequently delivering a sustained dose of a particular drug. See "Creating New Supramolecular Materials by Architecture of Three-Dimensional Nanocrystal Fiber Networks," *J. Am. Chem. S.* 124 (50): 15055-15063 (2002). Although structures appear to have been produced using L-DHL, they were not degradable in the body and consequently are of limited use as drug delivery matrices.

Condensed phosphates such as pyro- ($P_2O_7^{4-}$) and polyphosphates ($P_nO_{3n+1}^{(n+2)-}$) have been shown to play important roles in the control of biomineralisation and certain metabolic pathways. Pyrophosphates, for example, are known inhibitors of hydroxyapatite (HA) crystallisation and have been proposed to play an important role in the regulation of biomineralisation through interaction with alkaline phosphatase (ALP) and nucleoside triphosphate. It is thought that ALP catalyses the cleavage of the P—O—P bridge in the pyrophosphate molecule, which results in the production of $PO_4^{3-}$ and subsequent localised supersaturation leading to the precipitation of HA. There is evidence that suggests ALP is able to act on solid pyrophosphate salts, thus increasing the rate at which they may be dissolved. In one study, fluoroscein isothiocyanate conjugated ALP was used to investigate whether bovine intestinal ALP absorbed to the surfaces of dicalcium pyrophosphate dihydrate crystals. See Shinozaki et al., "Calcium Pyrophosphate Dihydrate (CPPD) Crystal Dissolution by Alkaline-Phosphatase—Interaction of Alkaline-Phosphatase on Cppd Crystals," *J. of Rheumatology,* 22(1) 117 (1995). This study described the localization of the enzyme on the surfaces of the crystals around etch-pits, which showed that the alkaline phosphatase was directly involved in calcium pyrophosphate dissolution. The apparent instability of $P_2O_7^{4-}$ anions and salts in the presence of ALP (an enzyme synonymous with the formation of new bone), suggests that pyrophosphate salts have great promise as resorbable biomaterials and for localised release of phosphate ions and drugs.

Amorphous calcium pyrophosphates were first reported in the literature in 1963, but remained little researched until they were identified in a particular species of barnacle (*Tetraclita squamosa*). The amorphous granular deposits that were reported were thought to act as a sink for toxic ions in the water, as barnacles have no hepatopancreas. In a more recent study, one group attempted to synthesize these amorphous granules and found that in order to maintain the amorphous state of the granular deposits, ions such as $Mn^{2+}$ had to be substituted into the structure of the granule. See Masala et al., "Modelling the Formation of Granules: the Influence of Manganese Ions on Calcium Pyrophosphate Precipitates," *Inorganica Chimica Acta,* 339:366-372 (2002).

SUMMARY OF THE INVENTION

This invention is based upon the unexpected discovery that fibrous calcium pyrophosphate particles can be prepared and stabilized.

In one embodiment, the present invention includes a composition comprising particles wherein the particles include fibers and the fibers include calcium and pyrophosphate, e.g., calcium pyrophosphate.

The present invention also includes methods for making a composition comprising particles wherein the particles include fibers and the fibers include calcium and pyrophosphate, e.g., calcium pyrophosphate. One method includes mixing a solution (e.g., an aqueous solution) of a calcium salt with a solution (e.g., an aqueous solution) of a pyrophosphate salt, pyrophosphoric acid, or combination thereof and recovering fibrous calcium pyrophosphate particles after a time sufficient for growth of fibrous calcium pyrophosphate particles. In one embodiment, the method further includes the step of stabilizing the recovered fibrous calcium pyrophosphate particles.

In another embodiment, the present invention includes a method for treating a patient, comprising administering to a patient (e.g., via the respiratory tract) a therapeutically effective amount of a pharmaceutical composition which includes fibrous calcium pyrophosphate particles and at least one pharmaceutically active ingredient.

In another embodiment, the present invention includes a pharmaceutical composition, comprising fibrous calcium pyrophosphate particles, at least one pharmaceutically active ingredient, and a pharmaceutically acceptable carrier.

The advantages of the particles of the present invention include a simple, low temperature (e.g., room temperature) synthesis, a narrow particle size distribution, the ability of the particles to act as a drug depot for sustained release of the pharmaceutically active ingredient, e.g., due to particle nanoporosity which also can reduces the density and aerodynamic diameter of the particles. In addition, the calcium pyrophosphate particles can be degraded in the body into nontoxic products.

BRIEF DESCRIPTION OF THE DRAWINGS

(FIG. 2B) Examination of the fibrous network revealed that the fibres were of approximately 20 nm in diameter. (FIG. 2C) An observation which was confirmed by transmission electron micrographs of calcium pyrophosphate particles. (FIG. 2D)

FIG. 4F shows the formation of crystals on the surface of the calcium pyrophosphate particles following a period of 24 hours immersion in double distilled water.

FIG. 7 includes a comparison between dexamethasone "free" (i.e., unloaded) and in untreated calcium pyrophosphate particles (0.0 mg SA).

DETAILED DESCRIPTION OF THE INVENTION

Figure 1A:
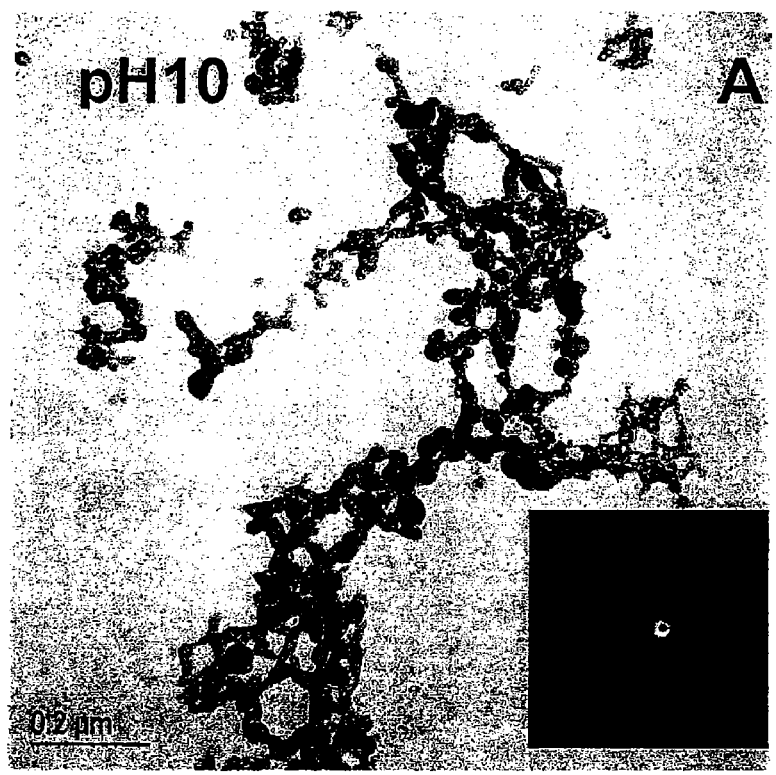
FIGS. 1A and 1B are transmission electron micrographs of calcium pyrophosphate precipitate formed from starting solutions at pH 10 (FIG. 1A) and pH 7 (FIG. 1B). In the inset of FIGS. 1A and 1B are electron diffraction patterns. The absence of spots or rings on the patterns indicates the amorphous nature of the precipitate when precipitated at both pH 7 and 10.

A description of example embodiments of the invention follows.

In one embodiment, the present invention includes a composition comprising particles wherein the particles include fibers and the fibers include calcium and pyrophosphate, e.g., calcium pyrophosphate. For example, the present invention includes a composition comprising fibrous particles of calcium pyrophosphate. The term "fibrous" is used herein to refer to particles formed from intertwined and/or self-assembled calcium pyrophosphate fibers (e.g., approximately 2 to 50 nanometers (nm) thick). In one embodiment, the fibrous calcium pyrophosphate particles are porous.

This invention demonstrates the significant change the morphology of a calcium pyrophosphate precipitate obtained by varying the pH of the precipitation conditions. Precipitates formed from starting solutions having a pH value of less than 7 consisted of a nanofiber network which self-organised into spherical particles. The particles, when gelled by compaction, facilitated the sustained release of macromolecules such as albumin into solution. The resulting bioresorbable material is useful as a drug delivery matrix.

In one embodiment, the calcium pyrophosphate particles are about 100 nm to about 1 micron (μm) in diameter. In another embodiment, the calcium pyrophosphate particles are about 1 μm to about 5 μm in diameter. In another embodiment, the calcium pyrophosphate particles are about 5 μm to about 10 μm in diameter. In another embodiment, the calcium pyrophosphate particles are about 10 μm to about 15 μm in diameter. In another embodiment, the calcium pyrophosphate particles are about 15 μm to about 20 μm in diameter. In another embodiment, the calcium pyrophosphate particles are about 20 μm to about 100 μm in diameter. In another embodiment, the calcium pyrophosphate particles are about 100 μm to about 5 millimeters (mm) in diameter.

In one embodiment, the fibrous calcium pyrophosphate particles form microscale assemblies. The fibrous calcium pyrophosphate particles can be porous.

In another embodiment, the fibers of calcium pyrophosphate are amorphous or nanocrystalline or both. As used herein, the term "amorphous" refers to a solid that is noncrystalline, having neither definite form nor structure. A crystalline solid, by contrast, is a homogeneous solid made up of a chemical compound throughout which the molecules are arranged in a regularly repeating pattern.

In another embodiment, a fatty acid can be added to the fibrous calcium pyrophosphate particles. For example, the composition of the invention can include oleic acid.

In another embodiment, a pharmaceutically active ingredient, for example, dexamethasone, can be added to the fibrous calcium pyrophosphate particles. As used herein, a "pharmaceutically active ingredient" is a compound that, when administered to a patient, improves the prognosis of the patient in need of treatment, e.g., delays the onset of and/or reduces the severity of one or more of the patient's symptoms associated with a disease, enables diagnosis, or provides a prophylactic benefit.

In another embodiment, the fibrous calcium pyrophosphate particles include a macromolecule, for example, a protein such as albumin. As used herein, the term "macromolecule" refers to a biological polymer such as a protein, a nucleic acid, or a polycarbohydrate. In one embodiment of the invention, the macromolecule is albumin.

In another embodiment, the fibrous calcium pyrophosphate particles include a chemical used to prevent opsonisation, for example, polyethylene glycol (PEG). As used herein, opsonisation is the process whereby particles are marked to be cleared by macrophages that remove foreign materials from the body. Pulmonary delivery particles may be coated with opsonisation inhibitors to retard the removal of the particles from the lung.

In some embodiments, the particles include a polymeric biomaterial or a combination of polymeric biomaterials. For example, polymeric biomaterials can be used to slow drug diffusion from the particles. Polymeric biomaterials include polymers and hydrogels. Examples of hydrogels include crosslinked alginates, chitosan, agar, non-fibrullar collagens, collagens, PEG, PAA (polyacrylic acid), HEMA (hydroxy ethyl methacrylate), modified celluolses (e.g., hydroxymethylcellulose). Examples of polymers include polyethylene (PE), PGA polyglycolic acid (PGA), poly lactic acid (PLA), polyurethanes (PU), polyhydroxybutyrate (PHB), and polytetrafluoroethylene (PTFE). Non-hydrogel polymers are also suitable for use in the present invention. Non-hydrogel polymers include, but are not limited to, polyurethane, polyester, polytetrafluoroethylene, polyethylene, polymethylmethacrylate, polysiloxanes, and poly hydroxyacids. Specific examples of non-hydrogel polymers include poly lactic acid, poly-L-lactic acid, poly-D,L-lactic acid, poly glycolic acid, poly-e-caprolactone, poly-p-dioxanon, tri-methylen carbonate, poly anhydrides, poly ortho ester, poly urethanes, poly amino acids, poly hydroxy alcanoates, poly phosphazenes, poly-b-malein acid, polyhydroxybutyrate, polystyrenes (e.g., poly(styrene-co-chloromethylsytrene)), lipids (e.g. monoolein), phospholipids, polyphosphoesters, polyphosphazenes, aliphatic polyesters (e.g., PCL PGA PLA and copolymers), PHB, PHV and copolymers, poly(1,4-butylene succinate), nylons, non-hydrogel polysaccharides (e.g., cellulose acetates), PEG-based polymers, poly(ethylene oxide), polyanhydrides, poly(butylene terephthalate), amphiphiles, fibrin, albumin, casein, keratin, fibrular collagen, silk fibroin, and polyhydroxybutyrate.

In another embodiment, the present invention includes a method of making particles of calcium pyrophosphate. The method comprises mixing a solution (e.g., an aqueous solution) of a calcium salt with a solution (e.g., an aqueous solution) of a pyrophosphate salt and recovering said fibrous calcium pyrophosphate particles after a time sufficient for growth of fibrous calcium pyrophosphate particles. In one embodiment, the method further includes stabilizing the recovered fibrous calcium pyrophosphate particles. As used herein, the "time sufficient for growth of fibrous calcium pyrophosphate particles" refers to a time during which the particles of the invention are allowed to form. In one embodiment of the present invention, the time sufficient for growth of the fibrous calcium pyrophosphate particles is at least about 1 minute such as at least about 5 minutes, between about 5 and about 45 minutes, or between about 15 and about 25 minutes, depending on reaction conditions.

In one embodiment of the present invention, the solution of a calcium salt is a calcium chloride solution, and the solution of a pyrophosphate salt is a sodium pyrophosphate solution.

In one embodiment of the present invention, the pH of the reagents is between pH 6 and 7. In another embodiment of the method of the present invention, the pH of the reagents is between pH 5 and 6.

pH of the reagents or mixtures of reagents can be altered using methods well known by those of ordinary skill in the art. For example, acids or bases can be added to change pH. In addition to adding acids or bases to change pH there are many indirect methods also well known to those of ordinary skill in the art such as, for example, by changing temperature, adding buffers, or changing pressure. In particular, changing the amount of a dissolved gas such as by changing temperature or pressure can be particularly effective, e.g., dissolved carbon dioxide gas forming carbonic acid or dissolved ammonia gas forming $NH_4OH$.

In one embodiment of the method of the present invention, the fibrous calcium pyrophosphate particles are recovered by filtration.

In one embodiment, stabilizing the fibrous calcium pyrophosphate particles includes heating the particles to more than 75° C., for example, to about 100° C. or to about 200° C. In another embodiment of the present invention, stabilizing the fibrous calcium pyrophosphate particles includes washing the particles with a polyphosphate solution, preferably sodium tripolyphosphate. In another embodiment, stabilizing the fibrous calcium pyrophosphate particles includes mixing the particles with a protein solution.

The present invention includes a pharmaceutical composition, comprising fibrous calcium pyrophosphate particles, at least one pharmaceutically active ingredient, and a pharmaceutically acceptable carrier. As used herein, a "pharmaceutical composition" is a formulation comprising the disclosed particles and a pharmaceutically acceptable diluent or carrier, in a form suitable for administration to a subject. The pharmaceutical composition can be in bulk or in unit dosage form. The unit dosage form can be in any of a variety of forms, including, for example, a capsule, an IV bag, a tablet, a single pump on an aerosol inhaler, or a vial. The quantity of active ingredient (i.e., a formulation of a therapeutic, diagnostic, or prophylactic compound or salts thereof) in a unit dose of composition is an effective amount and may be varied according to the particular treatment involved. It may be appreciated that it may be necessary to make routine variations to the dosage depending on the age and condition of the patient. The dosage will also depend on the route of administration. Routes include, but are not limited to, topical, oral, pulmonary, rectal, vaginal, parenteral, including transdermal, subcutaneous, intravenous, intramuscular, intraperitoneal and intranasal routes.

The compounds described herein, and the pharmaceutically acceptable salts thereof can be used in pharmaceutical preparations in combination with a pharmaceutically acceptable carrier or diluent. Suitable pharmaceutically acceptable carriers include inert solid fillers or diluents and sterile aqueous or organic solutions. The compounds can be present in such pharmaceutical compositions in amounts sufficient to provide the desired dosage amount in the range described herein. Techniques for formulation and administration of the compounds of the instant invention can be found in, for example, *Remington: the Science and Practice of Pharmacy*, 19$^{th}$ edition, Mack Publishing Co., Easton, Pa. (1995).

In another embodiment, the present invention includes a method for treating a patient, comprising administering to the patient (e.g., via the respiratory tract) a therapeutically effective amount of a pharmaceutical composition comprising fibrous calcium pyrophosphate particles and at least one pharmaceutically active ingredient. As used herein, a "patient" includes mammals, e.g., humans, companion animals (e.g., dogs, cats, birds and the like), farm animals (e.g., cows, sheep, pigs, horses, fowl and the like) and laboratory animals (e.g., rats, mice, guinea pigs and the like). In a preferred embodiment, the patient is human.

As used herein, a "therapeutically effective amount" of a compound is the quantity which, when administered to a patient in need of treatment, improves the prognosis of the patient, e.g., delays the onset of and/or reduces the severity of one or more of the patient's symptoms associated with a disease, enables diagnosis, or provides a prophylactic benefit. The amount of the compound to be administered to a patient will depend on the particular disease, the mode of administration, and the characteristics of the patient, such as general health, other diseases, age, sex, genotype, body weight and tolerance to drugs. The skilled artisan will be able to determine appropriate dosages depending on these and other factors. Effective amounts of the disclosed compounds typically range between about 0.1 mg/kg body weight per day and about 1000 mg/kg body weight per day, and preferably between 1 mg/kg body weight per day and 100 mg/kg body weight per day.

Particles of the present invention and/or fibers comprising the particles can have high specific surface area. This high specific surface area is thought to result from the nanoscale of the particles' fibers. Particles and/or fibers having high specific surface area have application in such areas as catalyst support, chromatography, and adsorption. In one embodiment, the fibrous calcium pyrophosphate particles of the present invention are useful to perform bioseparation. These particles, particularly when in the amorphous state, are able to accommodate numerous ionic substitutions. The fibrous calcium pyrophosphate particles can be used to extract toxic substances such as, for example, cadmium from solution, or can be used to remove particulate matter.

In other embodiments, the fibrous calcium pyrophosphate particles of the present invention are useful as insulators. It is believed that the fibrous calcium pyrophosphate particles of the present invention have improved insulative properties over other known materials. Without being held to any particular theory, this is believed to be due the nanoporous nature of the particles. In some embodiments, the particles are about 68% open volume. Further, the particles do not carry the risks that are associated with exposure to currently available insulating materials, because calcium pyrophosphate particles are sparingly soluble and non-toxic.

One of the major advantages of the fibrous calcium pyrophosphate particles over currently available technology is the particles are extremely simple and energy efficient to prepare, because it does not require a high temperature processing step and the by-products of the method can be relatively benign.

The present invention is based on a discovery of a means to produce particles (e.g., spheres or microspheres) of calcium pyrophosphate in the size range of about 1 μm to about 5 mm. These particles have a hierarchical structure and can be themselves composed of porous bundles of nanofibers. In some embodiments, the particles have a relative porosity of about 30 to about 90%. In one aspect, the particles have a specific surface area of about 35 to about 188 m$^2$/g. For example, in one embodiment, the particles have a relative porosity of about 68%, a density of about 0.77 g/cm$^3$, and a specific surface area of about 35 m$^2$/g. These porous structures can be used as depots from which to release therapeutic compounds in a sustained manner. The treatment of chronic asthma often relies on the delivery of hydrophobic steroids such as dexamethasone. Hydrophobic steroids have little affinity for ionic surfaces and therefore can be released rapidly (e.g., almost instantaneously) from calcium pyrophosphate surfaces. Non-toxic surfactant can also be used in the present invention to control the release of hydrophobic steroids. In vitro experiments have shown that the calcium pyrophosphate particles may be phagocytosed and dissolved intracellularly by macrophages. Thus, the calcium pyrophosphate particles may be cleared without harmful side effects from tissues such as the lung.

Parameters which are likely to alter particle characteristics are precipitation conditions such as temperature, pH, and concentration. These parameters can be altered to control particle size distribution and average particle size. In addition to controlling temperature, pH, and concentration, physical methods such as size selective membranes and sedimentation can be used.

EXEMPLIFICATION

Example 1

Figure 1B:
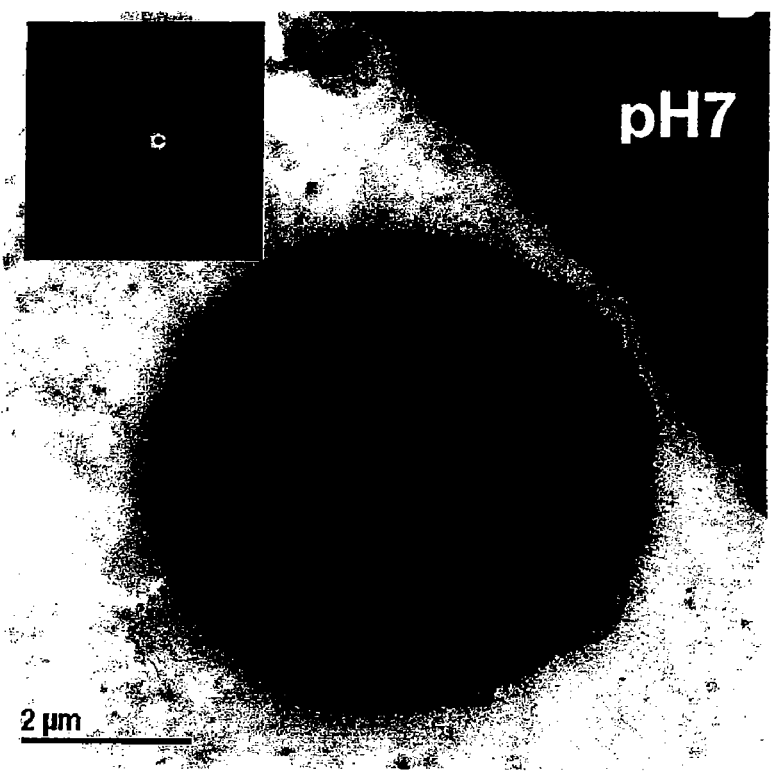

The synthesis of amorphous rather than crystalline materials is favored by the use of highly concentrated reagents, which are rapidly combined. This causes fast supersaturation of the solution and rapid precipitation which results in the formation of numerous nascent nuclei with little time or insufficient reactants to allow growth or ordering of the structure. Initial experimentation revealed that the highest concentration of $Na_4P_2O_7$ that was attainable in ambient conditions was 150 mM. Consequently, the precipitate was formed by the "one-time" addition of 500 mL $CaCl_2$ (300 mM) to 500 mL $Na_4P_2O_7$ (150 mM), which was filtered and washed using double distilled water and then acetone, before being dried at ambient temperature in a vacuum oven for 36 hours. Since pH can have a large influence on the morphology and compositions of precipitates, the pH of each solution was controlled using 1 M NaOH and 12 M HCl. When the pH value of each reagent solution was greater than 7, the precipitate remained in suspension and took more than one hour to filter. On examination, the precipitate consisted of an irregular globular precipitate, which was shown by selected area electron diffraction to be amorphous (FIG. 1A). When the pH of both reagents was reduced to less than or equal to 7, filtration proceeded as slowly as with the precipitate produced at a pH value greater than 7, however, after approximately 20 minutes the precipitate began to sediment from solution. Examination of the sediment using a light microscope revealed that the sedimented particles were spherical in morphology and of diameter 5-20 μg/m. Comparison of a transmission electron micrograph of one calcium pyrophosphate precipitate formed at pH 7 with one formed at pH 10, demonstrates the difference in the morphology of the amorphous calcium pyrophosphate precipitates (FIGS. 1A and 1B).

Figures 2A, 2B, 2C, 2D:
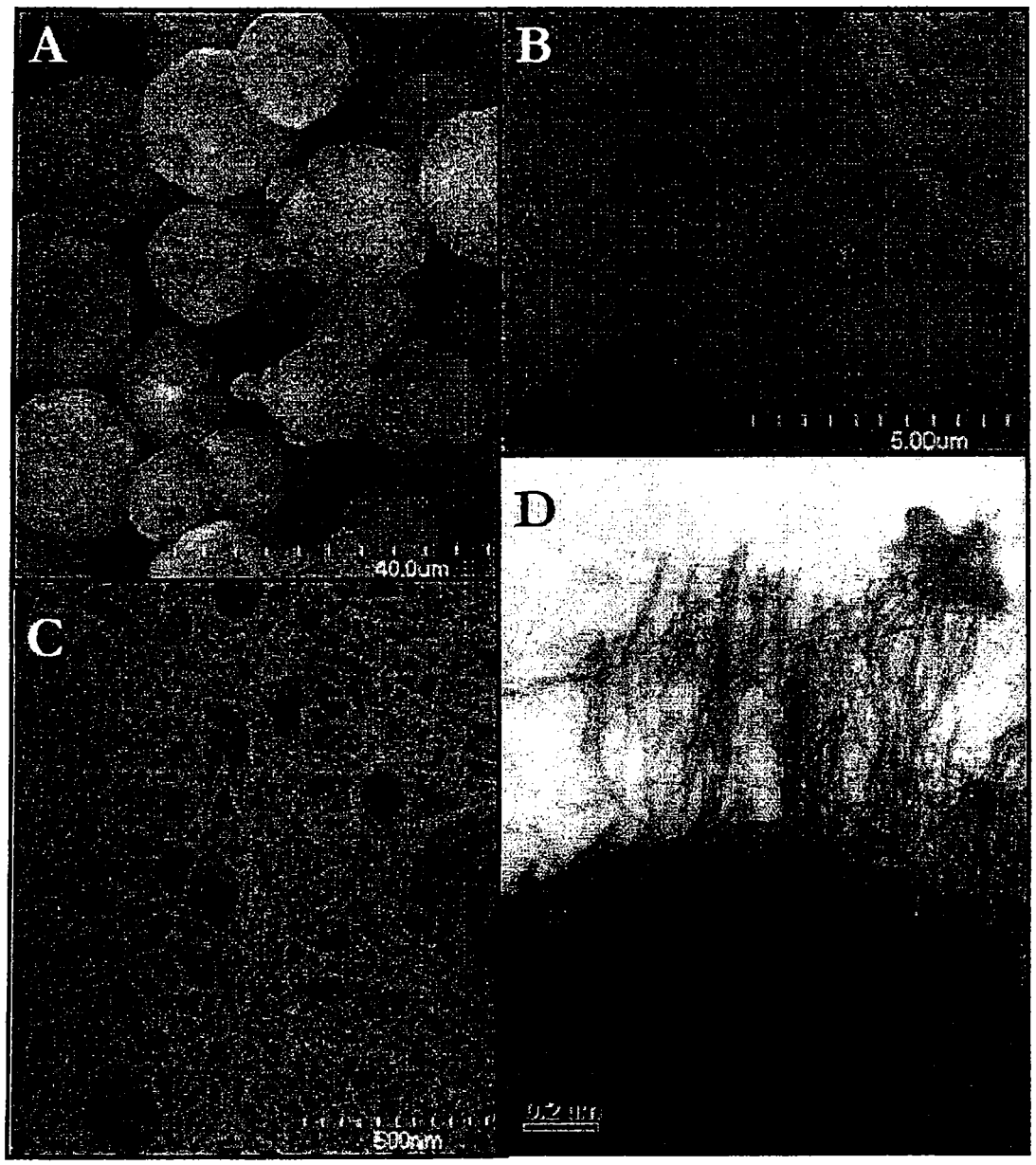
FIGS. 2A to 2D are scanning and transmission electron micrographs of calcium pyrophosphate precipitate. On sedimentation spherical particles formed ranging in diameter from 5 to 20 μm. Some of the particles were bonded and on closer inspection were shown to be attached through a fibrous network.
Figure 3:
FIG. 3 is a tilted cross section of a calcium pyrophosphate particle as revealed using focused ion beam milling. The homogeneity of the structure indicates that the fibers are distributed throughout the calcium pyrophosphate particles.

FIG. 2A shows a scanning electron micrograph of the precipitate, where the spherical structures exhibited particle diameters in the range of 5-20 μm and initially appeared to have agglomerated. Closer examination of the precipitate, however, indicated that the particles were not agglomerated but were conjoined (FIG. 2B). The joints between the individual particles were made by a network of fibres each of which was approximately 20 nm in diameter (FIG. 2C). When examined using a transmission electron microscope, fibres were observed to migrate from the surface of the fibrous network towards the electron beam. A calcium pyrophosphate sphere manipulated in this way is shown in FIG. 2D. Thus, an electron beam may be used to extract of fibres from the spherical structures. To determine whether the structure of the calcium pyrophosphate spheres was homogenous, they were mounted on an aluminium stub and a section was made using focussed ion beam milling. After milling, the samples were imaged using field emission gun scanning electron microscopy. A section cut through one of the calcium pyrophosphate spheres is shown in FIG. 3. The sphere was homogeneous throughout its structure, which suggests that the spherical calcium pyrophosphate particles did not form by growth from one nucleating point, but rather formed from aggregation of the fibrous networks in solution.

Figures 4A, 4B, 4C, 4D, 4E, 4F:
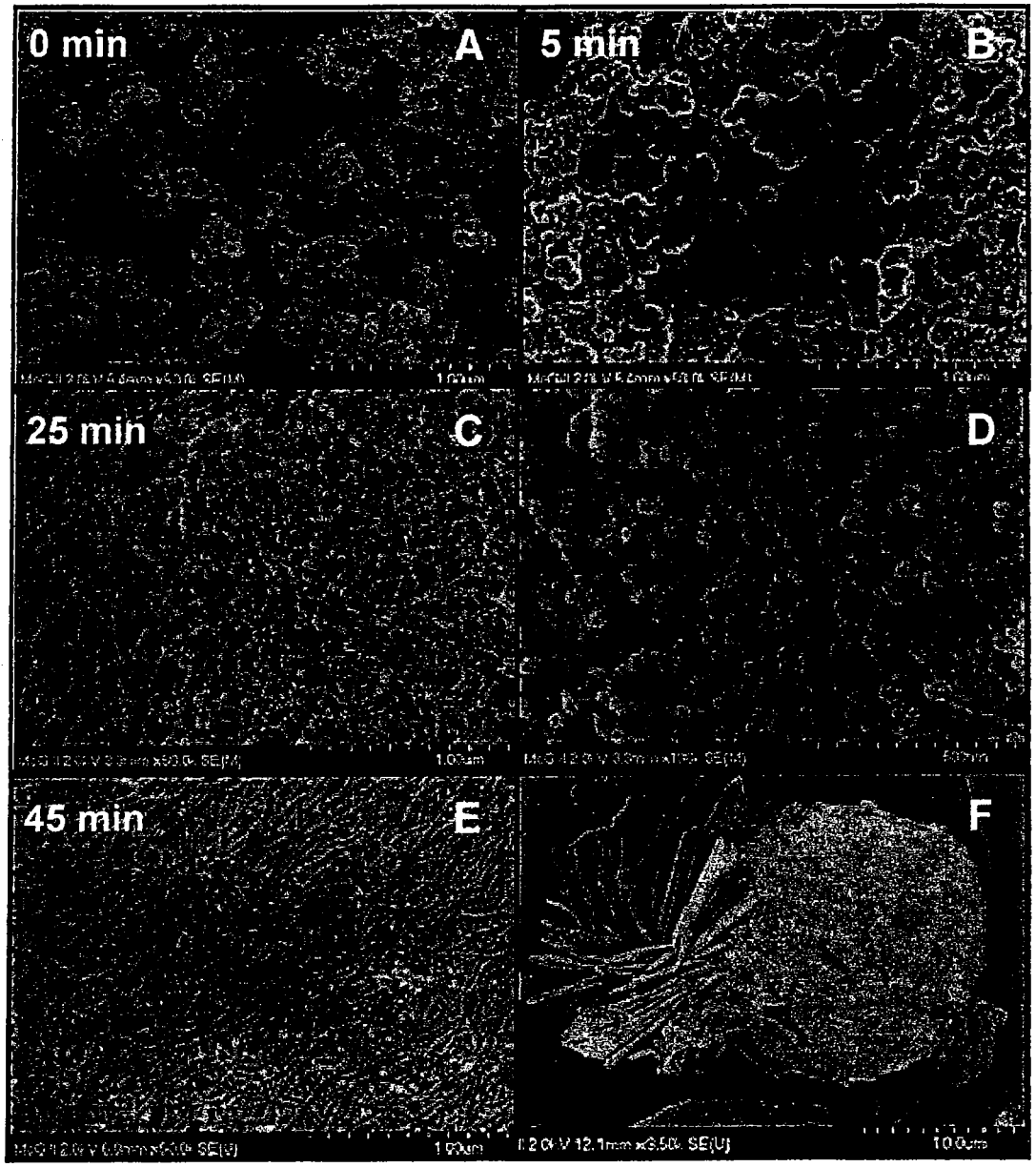
FIGS. 4A to 4F are photomicrographs of formation of calcium pyrophosphate particles. Images were captured at 0 min (FIG. 4A), 5 minutes (FIGS. 4B and 4C), 25 minutes (FIG. 4D) and 45 minutes (FIG. 4E) after combination of the $CaCl_2$ with the $Na_4P_2O_7$ solutions.

To investigate the mechanism by which the calcium pyrophosphate fibrous network was formed, the morphology of the precipitate was examined at various times following precipitation. After 0, 5, 25 and 45 minutes, a small quantity of the precipitate was immersed in excess (5 mL) acetone. The acetone was then evaporated at ambient temperature in a vacuum oven. The resulting powders were mounted on aluminium stubs and prepared for examination by field emission gun scanning electron microscopy. When immersed in acetone immediately following the combination of the two reactant solutions (0 minutes), the calcium pyrophosphate precipitate consisted of agglomerates of near spherical particles of approximate diameter 70 nm (FIG. 4A), similar in diameter and morphology to those reported by Masala et al., "Formation of Spherical Granules of Calcium Pyrophosphate," *Crystal Growth and Design*, vol. 3, 431 (2003). As time proceeded, the particles began to coalesce forming denser agglomerates of particles as illustrated by FIG. 4B (5 minutes after reaction). When examined 25 minutes following the start of the reaction, particles of approximately 70 nm (FIG. 4C) had begun to align parallel to one another (FIG. 4D), forming a fibrous calcium pyrophosphate network. At 45 minutes after initial reaction, the spherical particles were no longer evident, rather the precipitate consisted of intermeshed fibres of 20 nm diameter (FIG. 4E).

One of the major problems with utilising amorphous calcium salts is that they are inherently unstable. Amorphous calcium phosphate is so unstable that it has been shown to transform to hydroxyapatite in a vacuum and amorphous calcium carbonate is notoriously difficult to stabilise following manufacture. In the case of the amorphous calcium pyrophosphate described here, after a 24 hour immersion in double distilled water the spheres began to form dicalcium pyrophosphate dihydrate (DCPPD) crystals (FIG. 4F). Several compounds have been shown to stabilize amorphous calcium salts including pyrophosphate and magnesium ions. In the case of the amorphous calcium pyrophosphate precipitate reported here, the use of magnesium alone seemed to have little or no affect on the period of time that it took for crystallisation of the amorphous calcium pyrophosphate precipitate to occur. To address the problem of instability, a number of methods were screened of which heat treatment and washing with sodium tripolyphosphate were found to be the most simple and effective, but other techniques could also be used. Heating the calcium pyrophosphate fibre network to below crystallisation temperature (530° C.), as determined by thermo-gravimetric-analysis differential-thermal-analysis (TGA-DTA) measurements (FIGS. 5A and 5B) stabilized the precipitate in double distilled water for a period of seven days without causing any significant microstructural change to the precipitate. Another method of stabilization, without microstructural modification involved washing the amorphous calcium pyrophosphate precipitate with 500 mL of 10 mM sodium tripolyphosphate solution and then double distilled water. The sodium tripolyphosphate treatment stabilised the spheres for a period of 6 days before crystallisation occurred in distilled water. Sodium tripolyphosphate is used to prevent the formation of mineral in drinking water. It does this by binding strongly to mineral surfaces and preventing crystal growth. Without being held to any particular theory, it is believed that it stabilised the amorphous calcium pyrophosphate precipitate in a similar fashion. A third method of stabilization of the amorphous calcium pyrophosphate precipitate is mixing the precipitate particles with a protein solution, as described below.

Figure 5A:
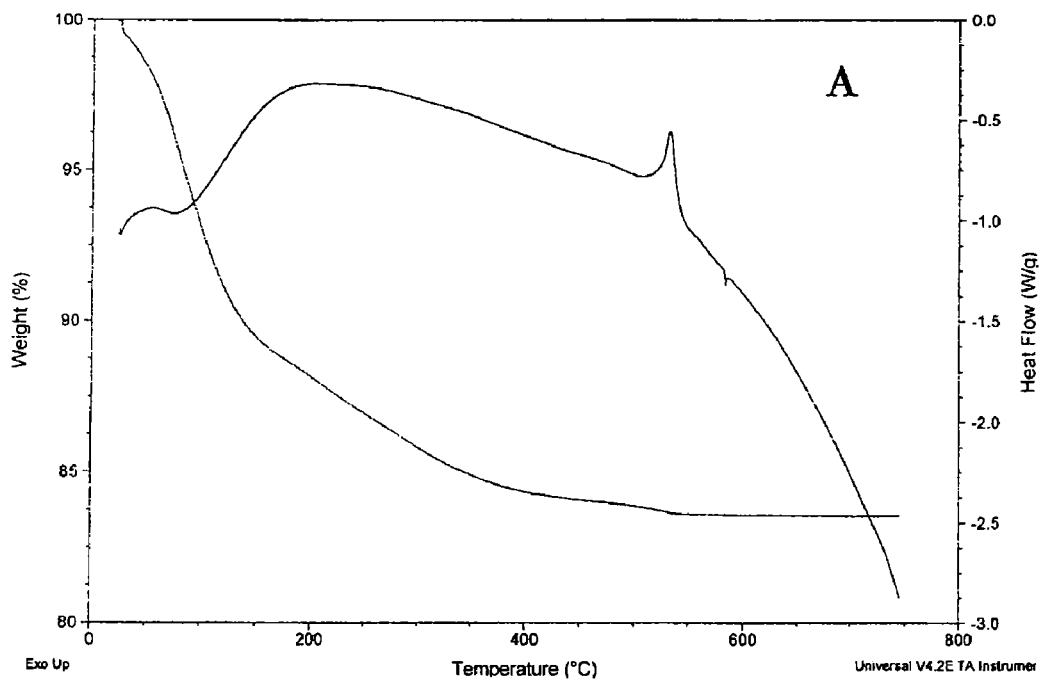
FIGS. 5A and 5B are a DTA/TGA plot (FIG. 5A) showing thermal crystallisation of the calcium pyrophosphate spheres when heated at a rate of 5° C./min and x-ray diffraction patterns (FIG. 5B) collected from amorphous calcium pyrophosphate during heating from ambient temperature to 550° C. Crystallization was observed at 550° C.
Figure 5B:
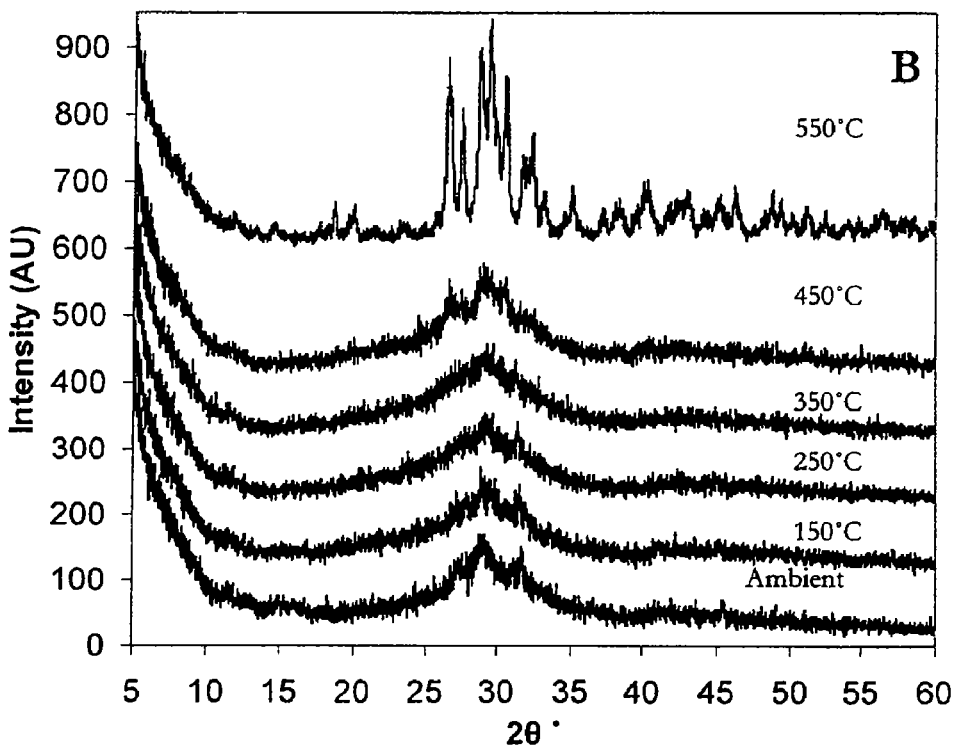

FIG. 5A shows a TGA/DTA plot for the amorphous calcium pyrophosphate precipitate (formed at a pH value of 7). As the precipitate was heated there was a steady weight loss and by 500° C. the precipitate had lost 16% of its original mass. Further heating of the precipitate to approximately 530° C. resulted in an exothermic event, which could be attributed to crystallisation of the amorphous/poorly crystalline calcium pyrophosphate to crystalline $\beta$-$Ca_2P_2O_7$ (FIG. 5B).

Figure 6:
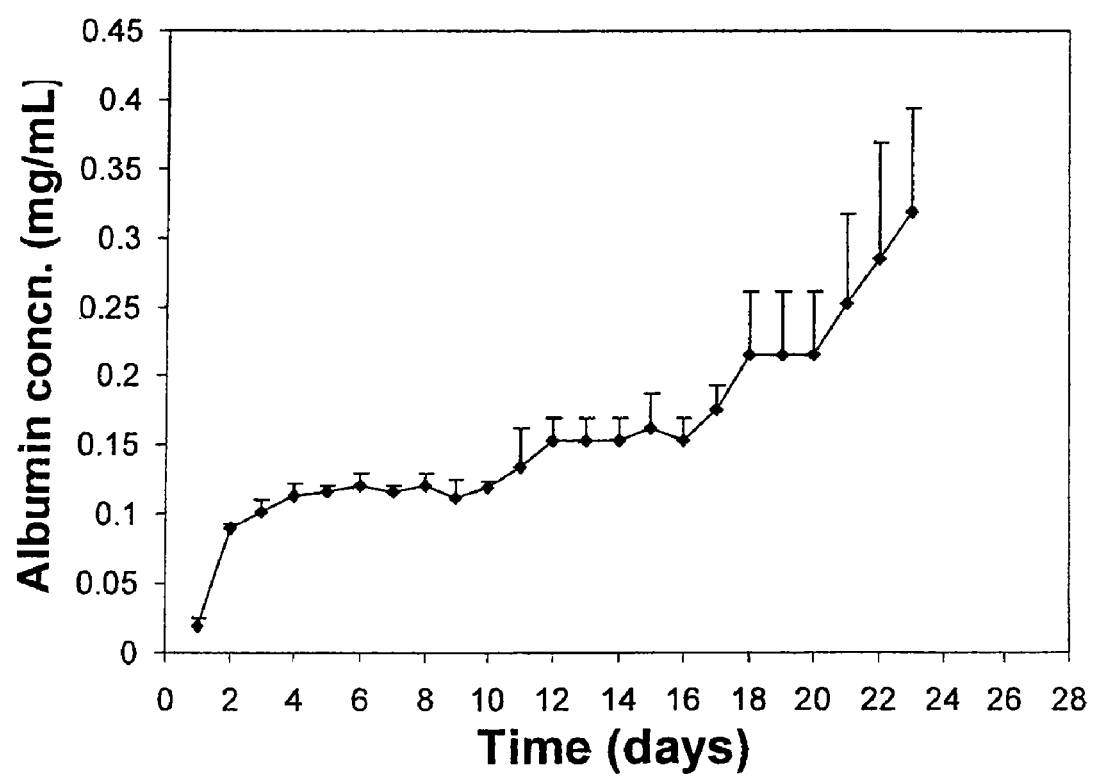
FIG. 6 is a plot of the concentration of albumin in an ageing medium in which calcium pyrophosphate gel was immersed over a period of 24 days. Albumin concentration was determined by comparing the absorbance of the solution at 280 nm with a calibration curve.

To form a functional material from the amorphous calcium pyrophosphate fibrous networks, 250 mg of the amorphous calcium pyrophosphate powder were combined with 500 µL of 80 mg/mL albumin to form a paste. The paste was then placed into a split mould and compacted to a pressure of 120 MPa for a period of ten minutes to form a gel. After this time the resulting gel was removed from the mould and washed thoroughly with double distilled water. The gel compact (nominally 8 mm diameter, 2 mm height) was placed into 8 mL double distilled water. The release of albumin from the structure was determined by measuring the absorbance of the double distilled water at 280 nm. The release profile from the calcium pyrophosphate gel is shown in FIG. 6. There was an initial release of sufficient albumin from the calcium pyrophosphate gel to cause in increase in concentration of the ageing solution to 0.1 mg/mL in the first day of the study. This increase may be attributed to the removal of albumin bound to the outer surface of the gel following manufacture. After this point, the release of albumin from the structure was steady up to 16 days of ageing, when there was a rapid increase in albumin concentration with a final albumin concentration in the ageing medium of 0.4 mg/mL. From true density and geometric measurements of control samples (with no albumin), it was found that the gels consisted of around 40% porosity. The incorporation of albumin into this pore space may have allowed the steady release of albumin into the solution through the nanopore structure of the gel. The sustained release of albumin from the pore space of the fibrous calcium pyrophosphate particles is a significant advantage of the disclosed invention.

Figure 7:
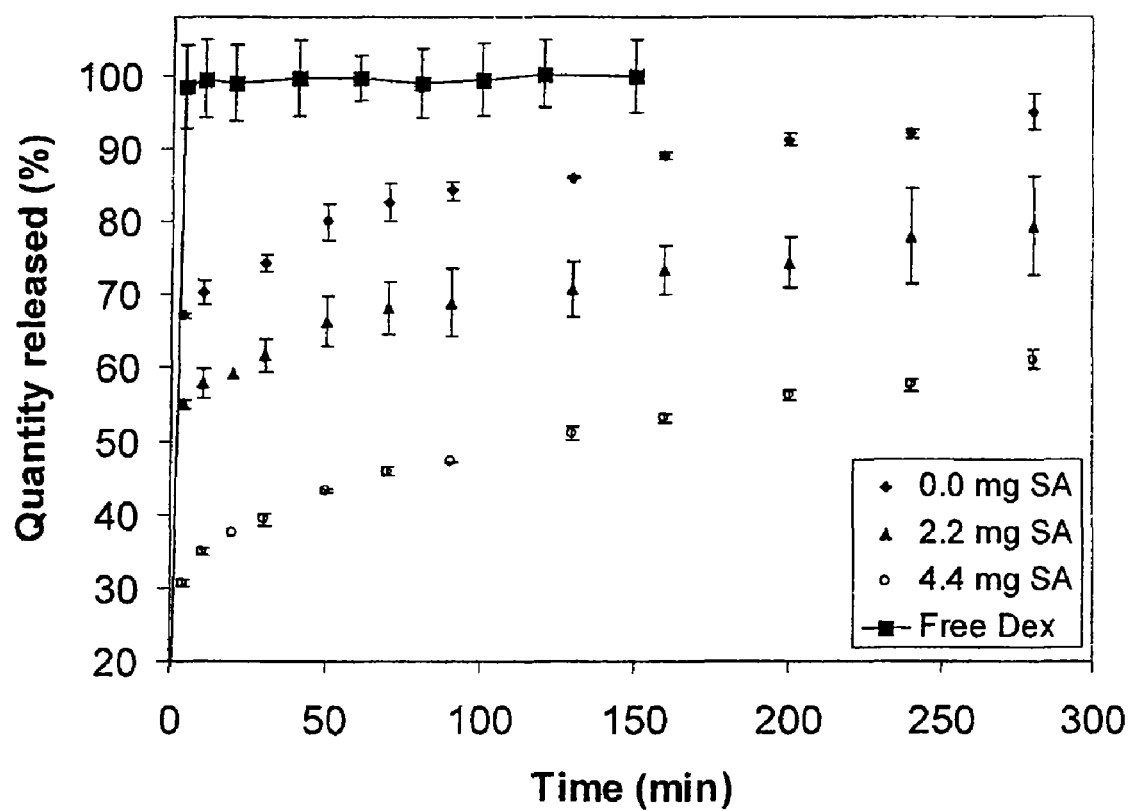
FIG. 7 is a plot of the release profiles of dexamethasone loaded into microspheres with increasing amounts of surfactant (SA), showing a corresponding reduction in the rate of release.

In order to investigate the capacity of the fibrous calcium pyrophosphate particles to provide sustained release of a pharmaceutically active ingredient, 150 mg of the particles were soaked in an alcoholic solution of 1.5 mg dexamethasone in 500 µl. This solution was allowed to evaporate in a vacuum oven at 30° C. to give 1 weight percent loading of dexamethasone in the particles. Although the aqueous solubility of dexamethasone is very low (88 µg/ml) it is very much higher than that required for a therapeutic effect. About 65% of the dexamethasone was released within 4 minutes. However, when oleic acid, a non-toxic surfactant, was combined with the drug at a 4.4:1 ratio, this initial release could be reduced to 30%, with only 60% being released in 5 hours. From FIG. 7, it is evident that the fibrous calcium pyrophosphate particles conferred a diffusion control on the dexamethasone release, because free dexamethasone dissolved completely within a few minutes. This experiment demonstrates the application of surfactant-treated fibrous calcium pyrophosphate particles as controlled release depots.

Example 2

This example describes the effects of concentration and pH in forming fibrous calcium pyrophosphate particles.

Figure 8A:
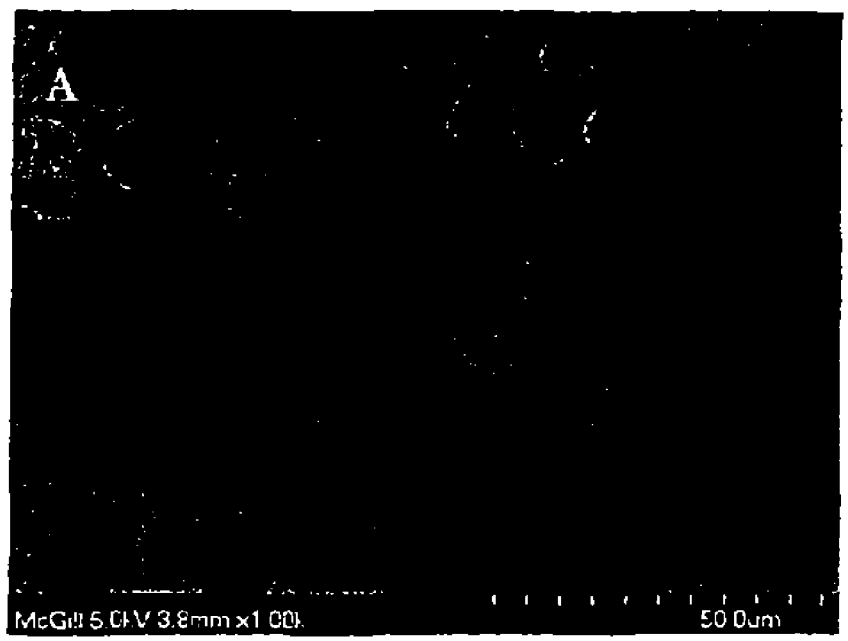
FIGS. 8A and 8B are photomicrographs of fibrous calcium pyrophosphate particles according to one embodiment of the present invention.
Figure 8B:
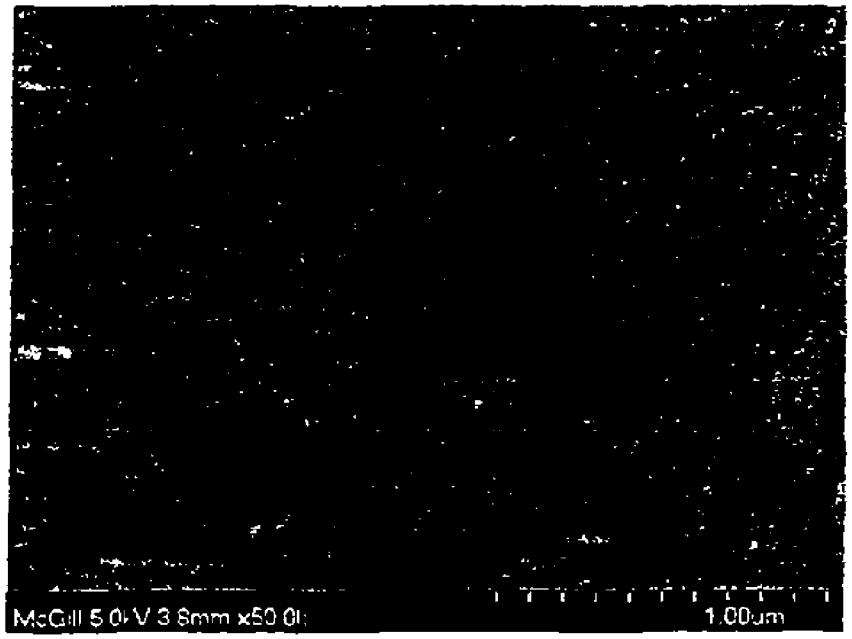

An initial mixture of equal volumes of a 300 millimolar (mM) aqueous calcium chloride ($CaCl_2$) ($CaCl_2$ obtained from Fisher Scientific, Cat. No. C77-500) solution and a 150 mM aqueous tetrasodium pyrophosphate ($Na_4P_2O_7$) ($Na_4P_2O_7.10H_2O$ obtained from Sigma Aldrich, Cat. No. P8010-500) solution was prepared and had an initial pH of approximately 6.6 (without any prior adjustment of the pH of the starting solutions) and formed a milky white precipitate similar to that described in Example 1. The pH of the initial mixture was lowered to 4.2 with 1 molar (M) hydrochloric acid (HCl) and fibrous calcium pyrophosphate particles formed over 2 hours at room temperature. FIGS. 8A and 8B are photomicrographs of the fibrous calcium pyrophosphate particles.

As the pH of the initial mixture was reduced from 6.6 to 5 or more, no fibrous calcium pyrophosphate particles formed and the milky white precipitate remained. In instances when the pH of the initial mixture was reduced to below pH 2.7, no fibrous calcium pyrophosphate particles formed. When the calcium chloride and tetrasodium pyrophosphate solutions concentrations were both halved (to 150 mM and 75 mM, respectively) and used to form the initial mixture, the pH below which no fibrous calcium pyrophosphate particles formed was pH 3.

If the pH is raised above these lower pHs, 2.7 and 3, below which no fibrous calcium pyrophosphate particles formed, e.g., by dilution by addition of an equal volume of water, relatively small fibrous calcium pyrophosphate particles formed very quickly (within minutes). Whereas raising the pH to 4.2 by addition of alkali caused the fibrous calcium pyrophosphate particles to form slowly, about 2 hours. Generally smaller fibrous calcium pyrophosphate particles were formed towards the lower "boundary" pH of 2.7 than the higher "boundary" pH of 4.2. Other methods to raise pH include the addition of non aqueous solvents such as ethanol.

When 600 mM calcium chloride and 300 mM tetrasodium pyrophosphate solutions (both pH 7 prior to mixing) were used to form the initial mixture, no change in fibrous calcium pyrophosphate particle size was noted compared to when 300 mM calcium chloride and 150 mM tetrasodium pyrophosphate solutions were used to form the initial mixture.

However, when 150 mM calcium chloride solution and 75 mM tetrasodium pyrophosphate solution, both adjusted to pH 7, were used to form the initial mixture, very small fibrous calcium pyrophosphate particles with a diameter of about 1 to 3 microns were formed. Similar results were obtained when 75 mM calcium chloride solution and 37.5 mM tetrasodium pyrophosphate solution were used to form the initial mixture.

In various experiments, particles formed from an amorphous phase produced by mixing calcium and pyrophosphate solutions (i.e., 300 mM aqueous calcium chloride solution and 150 mM aqueous tetrasodium pyrophosphate solution or, half that concentration, 150 mM aqueous calcium chloride solution and 75 mM aqueous tetrasodium pyrophosphate solution). Fibrous particles formed below pH 4, but not above pH 5 (at pH of 5 or more, microcrystals formed from the amorphous phase). Between pH 4 and 5, particles formed that were mixed with an amorphous phase but nanofibrous microparticles appeared to crystallize rapidly in the presence of the amorphous phase.

When fibrous particles (10 mg) made as detailed in above in this Example were stored in 5 mL phosphate buffered saline (PBS) (PBS tablets, without calcium and without magnesium, were obtained from Fisher Scientific, Cat. No. 2810305) made as per manufacturer's instructions no crystallisation of the particles was observed after 4 days at room temperature.

Example 3

This example describes the effects of changing the calcium to phosphate ratio (the "$Ca/P_2O_7$ ratio") forming fibrous calcium pyrophosphate particles.

An initial mixture of equal volumes of a 600 mM aqueous calcium chloride solution (pH 7) and a 150 mM aqueous tetrasodium pyrophosphate solution (pH 7) was prepared. Fibrous calcium pyrophosphate particles formed in the mixture. No change in the appearance of the calcium pyrophosphate particles was noted as compared to calcium pyrophosphate particles formed from a mixture of 300 mM aqueous calcium chloride and 150 mM aqueous tetrasodium pyrophosphate solutions.

A second initial mixture of equal volumes of a 150 mM aqueous calcium chloride solution (pH 7) and a 150 mM aqueous tetrasodium pyrophosphate solution (pH 7) was prepared. An amorphous phase and calcium pyrophosphate particles in a range of sizes were formed.

Example 4

This example describes the use of filtrates to form additional fibrous calcium pyrophosphate particles.

Most filtrates obtained from preparations of the calcium pyrophosphate particles (e.g., filtrates of the fibrous calcium pyrophosphate particles of Examples 2 and 3) precipitated more particles within the 40 minutes after filtering the particles. Precipitation of calcium pyrophosphate particles from filtrates was accelerated in some cases by adding a small quantity of ethanol (ethanol, 90.65% obtained from Fisher Scientific, Cat. No. A9954).

Example 5

This example describes experimental studies of the stability of fibrous calcium pyrophosphate particles.

In general, the stability of the sphere particles depended on the size of the calcium pyrophosphate particles. The particles formed from an initial mixture of 300 mM calcium chloride and 150 mM tetrasodium pyrophosphate solutions as described in Example 2 were filtered and added to water with adjustment to pH 7. The particles were stable for several days in water at room temperature.

Smaller particles formed from an initial mixture of 150 mM calcium chloride and 75 mM tetrasodium pyrophosphate solutions, also described in Example 2, were filtered and added to water. These particles were unstable in water (at room temperature) and changed very quickly (within 2 hours) to a crystalline phase.

Additional experiments with calcium pyrophosphate particles prepared from various initial mixtures showed that the water is not suitable to keep particles stable in solution. In each case, particles were filtered and added to water. The initial pH of the water/particle composition was varied from 2.8 to 10. After about 18 hours at room temperature, the pH of water/particle composition of each of these trials was between 3.9 to 4.7.

In one experiment, calcium pyrophosphate particles made from an initial mixture of 300 mM aqueous calcium chloride solution and a 150 mM aqueous tetrasodium pyrophosphate solution, as described supra, were dried for 2 hours at 200° C. The dried particles were added to water (0.1 gram of particles in 5 milliliters (mL) of water) and presented good stability in water at room temperature for at least 13 days.

In additional experiments, calcium pyrophosphate particles were dried for 1 hour at temperatures as low as 100° C. and then added to water. These particles also presented good stability in water at room temperature. Calcium pyrophosphate particles were also dried at 75° C. and then added to water. The particles dried at 75° C. changed to crystals in less than 24 hours and thus did not exhibit good stability.

In other experiments, calcium pyrophosphate particles made from an initial mixture of 300 mM aqueous calcium chloride solution and a 150 mM aqueous tetrasodium pyrophosphate solution, as described supra, were added to various chloride solutions and tetrasodium pyrophosphate solution for 42 days and stability at room temperature was assessed. Table 1 shows the effects of various storage media on stability of calcium pyrophosphate particles. The tetrasodium pyrophosphate solution/particle system was initially pH adjusted to 7.

TABLE 1

| Storage Medium | Storage Medium Concentration | Stability Observations |
| --- | --- | --- |
| Potassium chloride (KCl) | 2 molar (M) | Small amount of crystals formed from particles |
| Calcium chloride ($CaCl_2$) | 300 mM | Mixture of particles and crystals formed from particles |
| Sodium Chloride (NaCl) | 2 M | Particles completely changed to crystals |
| Tetrasodium pyrophosphate | 150 mM | Particles changed to crystals within 1 hour |

Example 6

This example describes production of calcium pyrophosphate particles from calcium chloride and sodium tripyrophosphate solutions.

Figure 9:
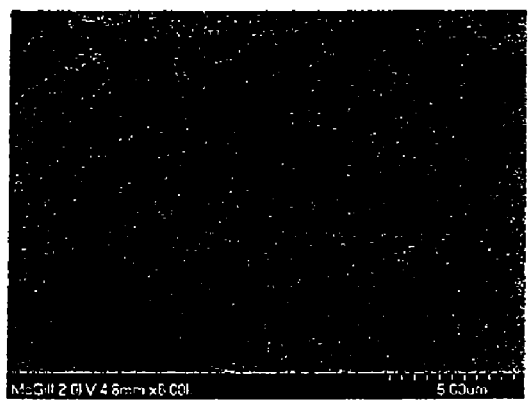
FIG. 9 is a photomicrograph of calcium pyrophosphate particles formed from calcium chloride and sodium tripyrophosphate solutions according to one embodiment of the present invention.

A 300 mM aqueous calcium chloride solution and a 150 mM aqueous sodium tripolyphosphate ($Na_5P_3O_{10}$) ($Na_5P_3O_{10}$ obtained from Sigma Aldrich, Cat. No. T-5883-500) were individually adjusted to pH 7. An initial mixture of equal volumes of each pH-adjusted solution was then prepared. The initial mixture was left to stand at ambient temperature. One and one-half hours after mixing, spherical, white particles began to appear. Formation of the particles continued until 5 hours post-mixing. FIG. 9 is a photomicrograph of the obtained particles. From the photomicrograph, the particles appear to have a petal-like or plate-like structure.

Example 7

This example describes production of calcium pyrophosphate particles from various solutions containing calcium and pyrophosphate ions.

Equal volumes of a 300 mM aqueous calcium acetate (Ca ($C_2H_3O_2)_2$) ($Ca(C_2H_3O_2)_2 \cdot H_2O$ obtained from Fisher Scientific, Cat. No. S79940) solution and a 300 mM aqueous calcium chloride solution were mixed and the resulting mixture was mixed in equal volume proportion with a 150 mM aqueous tetrasodium pyrophosphate solution (pH 7) to form an initial mixture. The pH of the initial mixture was lowered to 3.5 with 1 M HCl and small fibrous calcium pyrophosphate particles formed at room temperature.

Equal volumes of a 300 mM aqueous calcium acetate solution and a 150 mM aqueous tetrasodium pyrophosphate solution (pH 7) were mixed to form an initial mixture. The pH of the initial mixture was lowered to 3.5 with 1 M HCl and small fibrous calcium pyrophosphate particles formed at room temperature.

Equal volumes of a 300 mM aqueous calcium chloride solution (pH 7) and a 150 mM aqueous dipotassium pyrophosphate ($K_2P_2O_7$) solution (pH 7) were mixed to form an initial mixture. The pH of the initial mixture was lowered to pH 3.5 with 1 M HCl and small fibrous calcium pyrophosphate particles formed after 45 minutes at room temperature.

Based on the above-described experimental results, the counterions for calcium and pyrophosphate did not seem to be an important factor in the preparation of small fibrous calcium pyrophosphate particles.

Example 8

This example describes production of calcium and magnesium pyrophosphate particles.

Figure 10A:
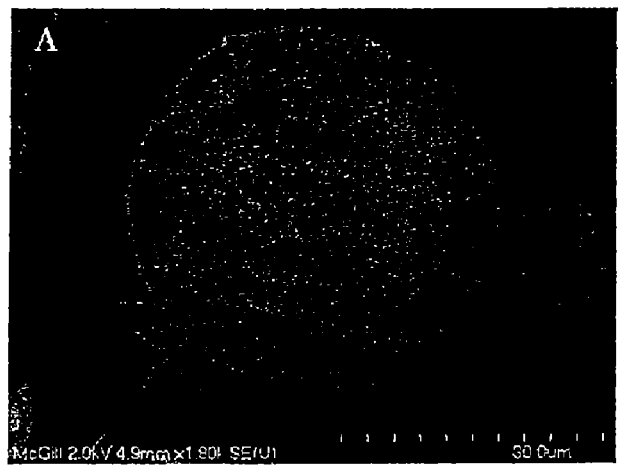
FIGS. 10A and 10B are photomicrographs of a precipitate which included small fibrous calcium and magnesium pyrophosphate particles according to one embodiment of the present invention.
Figure 10B:
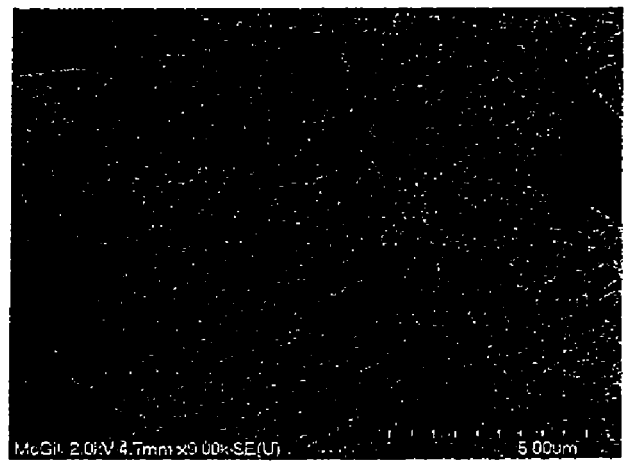

A 300 mM aqueous magnesium chloride ($MgCl_2$) ($MgCl_2 \cdot 6H_2O$ obtained from Fisher Scientific, Cat. No. M33-500) solution (pH 7) and a 300 mM aqueous calcium chloride solution (pH 7) were mixed to produce a mixture with a cation concentration of 300 mM and having a Ca/Mg ion ratio of 2. Then, this mixture was mixed in equal volume proportion with a 150 mM aqueous tetrasodium pyrophosphate solution (pH 7) to form the initial mixture. A precipitate formed at room temperature. The precipitate was left at room temperature for 13 days. FIGS. 10A and 10B are photomicrographs of the precipitate and show that the precipitate included small fibrous calcium and magnesium pyrophosphate particles and crystals. FIG. 10B shows a magnified view of the surface of the spherical particle of FIG. 10A. The fibers in FIG. 10B have cross-section with an approximately 500 nm diameter.

Example 9

This example describes production of pyrophosphate particles using ethanol.

Figure 11:
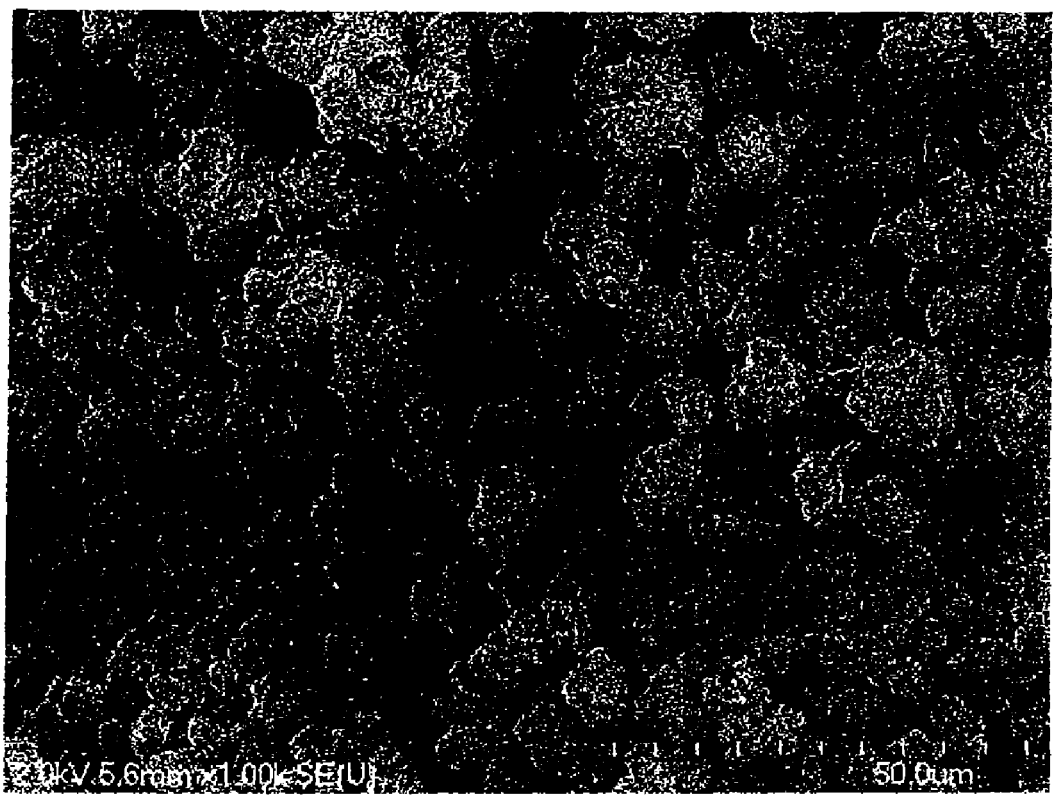
FIG. 11 is a photomicrograph of pyrophosphate particles formed using ethanol according to one embodiment of the present invention.

Equal volumes of ethanol and a 150 mM aqueous sodium pyrophosphate ($Na_2H_2P_2O_7$) ($Na_2H_2P_2O_7$ obtained from Sigma Aldrich, Cat. No. P8135-500) solution (pH 4.4) were mixed to form a mixture of pH 4.6. Small spherical clusters formed in the mixture. FIG. 11 is a photomicrograph of the small spherical clusters.

Example 10

This example describes production of calcium pyrophosphate particles.

Figure 12A:
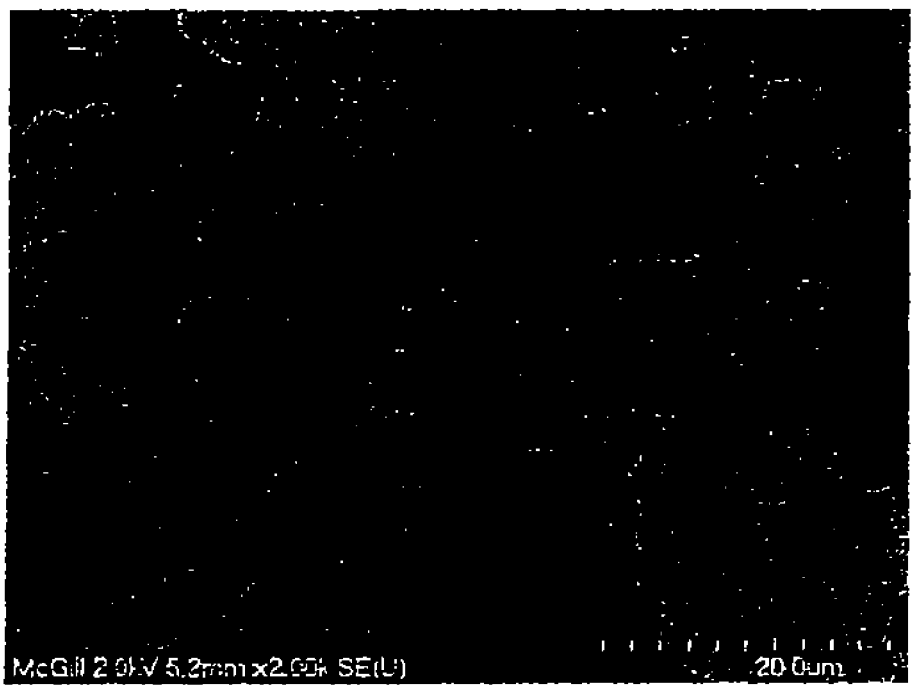
FIGS. 12A and 12B are photomicrographs of calcium pyrophosphate particles according to one embodiment of the present invention.
Figure 12B:
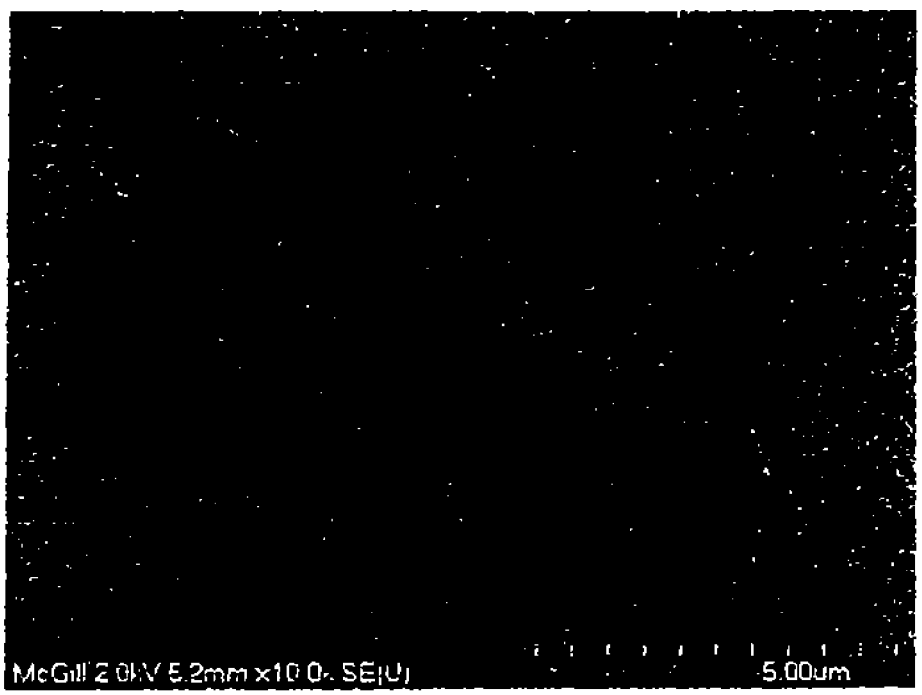

An initial mixture of equal volumes of a 300 millimolar (mM)) aqueous calcium chloride solution (pH 7) and a 150 mM aqueous sodium pyrophosphate solution (pH 4.4) was prepared and had an initial pH of approximately 3.0. No precipitation occurred in the initial mixture. Then, 1 M ammonium hydroxide ($NH_4OH$) ($NH_4OH$ obtained from Fisher Scientific, Cat. No. A669S212) was added to the initial mixture to increase the pH to 3.4 and precipitation began. The mixture was left at room temperature for 20 minutes, during which small spherical particles formed. FIGS. 12A and 12B are photomicrographs (SEM) of the obtained particles. FIGS. 12A and 12B show that the particles are not only small (about 2 microns) but also quite porous.

Example 11

This example describes production of calcium pyrophosphate particles.

Figure 13A:
FIGS. 13A and 13B are photomicrographs of calcium pyrophosphate particles according to one embodiment of the present invention.
Figure 13B:
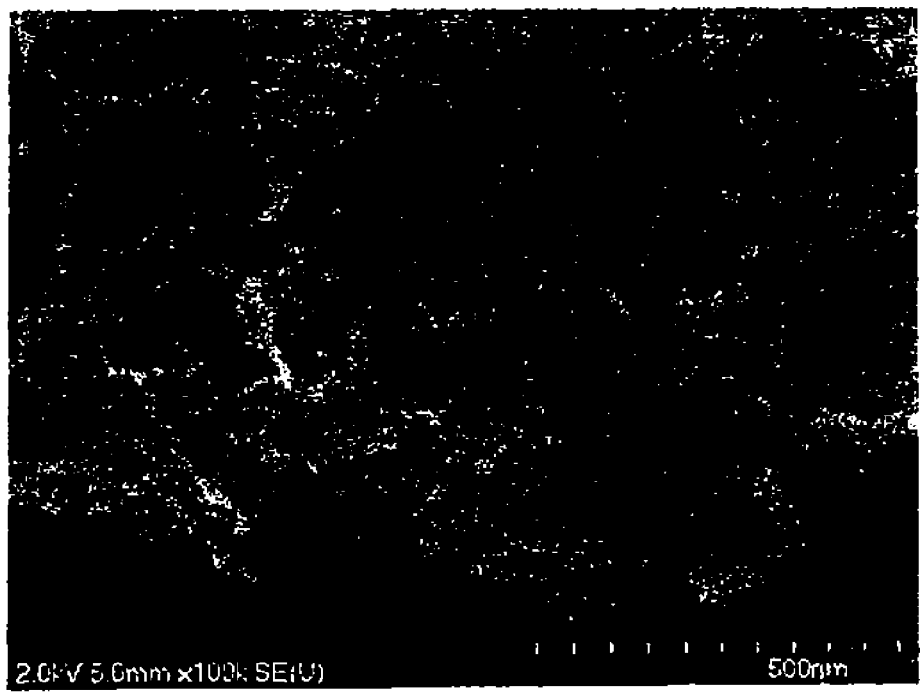

An initial mixture of equal volumes of a 300 mM aqueous calcium chloride solution (pH 7) and 150 mM pyrophosphoric acid ($H_4P_2O_7$) with a pH adjusted to 7 with 25% (vol) ammonium hydroxide was prepared. After 4 hours at room temperature, small spherical particles started to form slowly. After 18 additional hours at room temperature, small spherical particles were well formed and it appeared that some crystals had begun to form. FIGS. 13A and 13B are photomicrographs (SEM) of the obtained particles.

Particles were obtained when an aqueous polyphosphoric acid solution (poly phosphoric acid 105% from Thermphos, Batch No. D04 1700) (concentration 55.5 mg/ml) at pH 5 (adjusted with 5M NaOH) and calcium chloride aqueous solution (300 mM, no pH adjustment) were mixed. The fibrous particles formed after 4 hours. With an aqueous polyphosphoric acid solution of pH 7, only a milky white homogeneous precipitate was formed.

Particles were obtained from the mixture of aqueous superphosphoric acid solution (super phosphoric acid from Sigma Aldrich, Cat. No. 398608) with concentration of 55.5 mg/ml and pH 6.5 or pH 5.5 (adjusted with 5M NaOH) and $CaCl_2$ aqueous solution (300 mM no pH adjustment).

With a superphosphoric acid solution pH 5.5 (adjusted with 5M NaOH), fibrous particles formed after 3 hours 30 minutes and with a superphosphoric acid solution pH 6.5, fibrous particles formed after 5 hours.

With an aqueous superphosphoric acid solution of pH 7 only a milky white homogeneous precipitate formed.

With an aqueous superphosphoric acid solution of pH 3, there was no precipitation.

Example 12

This example describes production of calcium pyrophosphate particles using a solution of calcium chloride in ethanol.

An initial mixture of equal volumes of a 300 mM calcium chloride solution in ethanol and a 150 mM aqueous tetrasodium pyrophosphate solution (pH 7) was prepared. Spherical particles formed and appeared to resemble those formed from a purely aqueous precipitation as described in Example 2.

Figure 14:
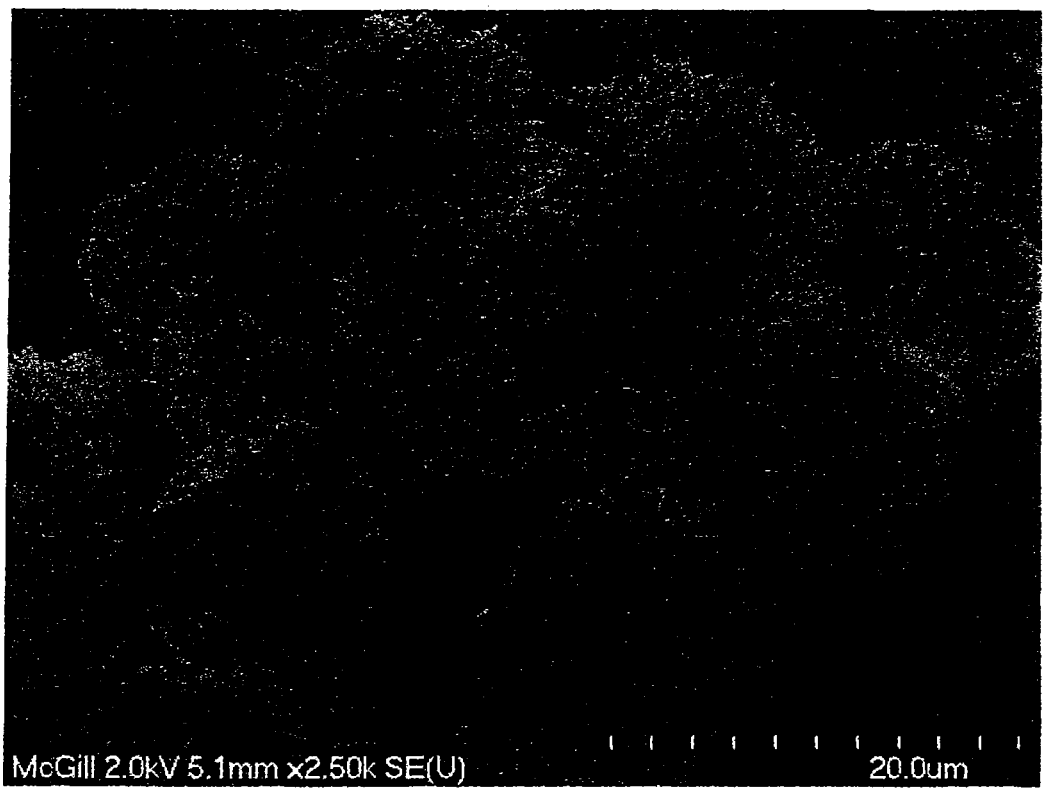
FIG. 14 is a photomicrograph of calcium pyrophosphate particles formed using a solution of calcium chloride in ethanol according to one embodiment of the present invention.

Another batch of particles was prepared by first forming a calcium chloride mixture by combining a 300 mM calcium chloride solution in ethanol with a 300 mM aqueous calcium chloride solution at a volume ratio of 2:3, respectively. A mixture of equal volumes of the calcium chloride mixture a 150 mM aqueous tetrasodium pyrophosphate solution (pH 7) was prepared. Spherical pyrophosphate particles formed. FIG. 14 is a photomicrograph of the obtained particles. The particles appeared to have a sponge-like morphology.

Figure 15A:
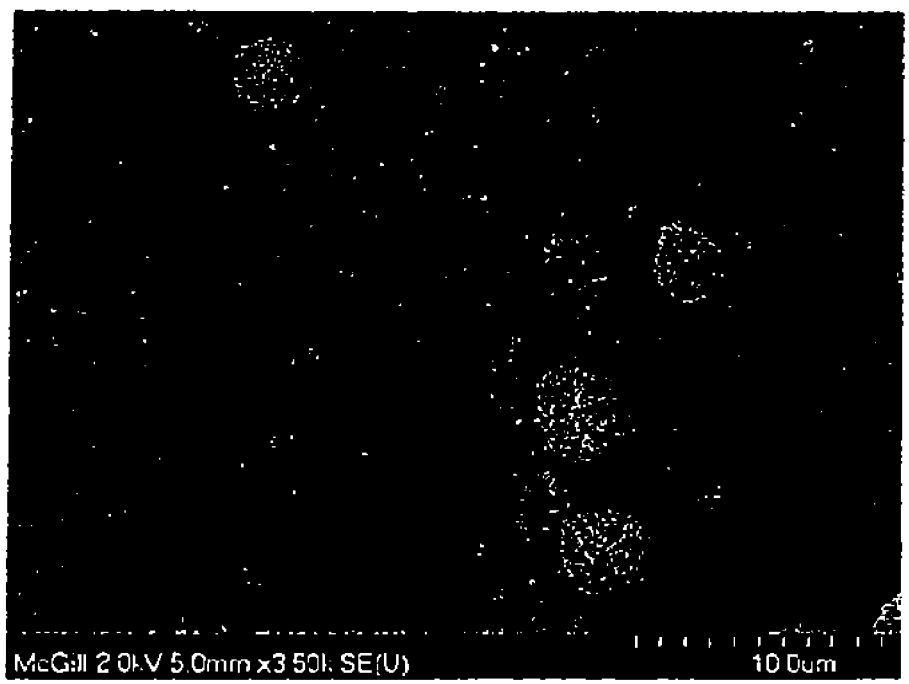
FIGS. 15A and 15B are photomicrographs of calcium pyrophosphate particles formed using ethanol according to one embodiment of the present invention.
Figure 15B:
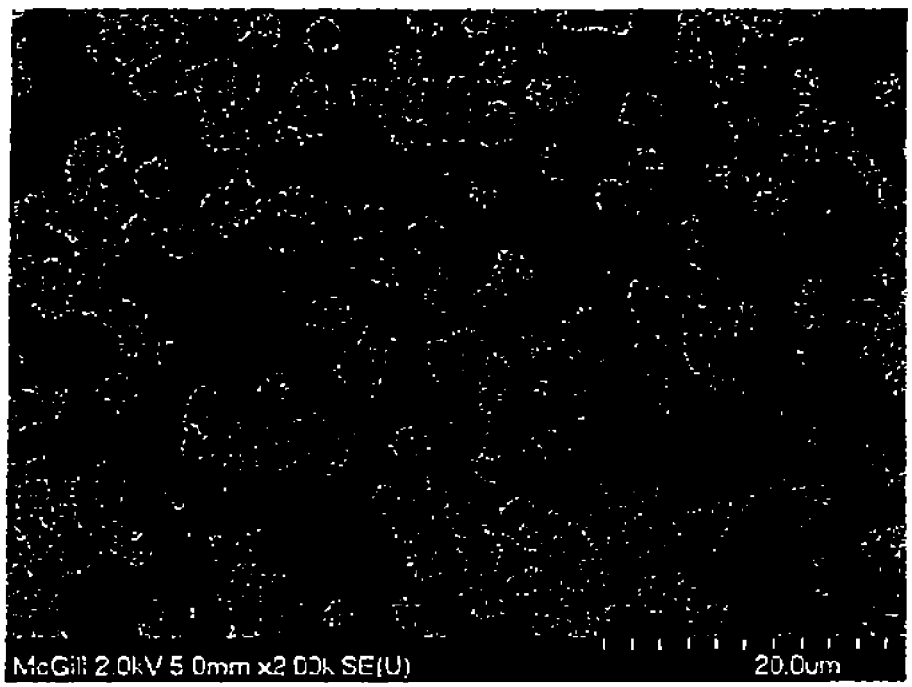

When ethanol was added to a mixture of equal volumes of a 300 mM aqueous calcium chloride solution and a 150 mM aqueous tetrasodium pyrophosphate solution before particle formation, it was observed that particles formed were very small (about 3 microns) and appeared to grow on the glass slide during isolation by evaporation rather than forming in the bulk solution. FIGS. 15A and 15B are photomicrographs of the obtained particles. FIG. 15A is a top view on the glass slide. FIG. 15B is a back view after being removed from the slide with adhesive tape.

Example 13

This example describes production of calcium pyrophosphate particles using saturated solutions of calcium chloride and sodium pyrophosphate in ethanol.

Figure 16A:
FIGS. 16A and 16B and 17A to 17D are photomicrographs of calcium pyrophosphate particles formed using saturated solutions of calcium chloride and sodium pyrophosphate in ethanol according to one embodiment of the present invention.
Figure 16B:
Figure 17A:
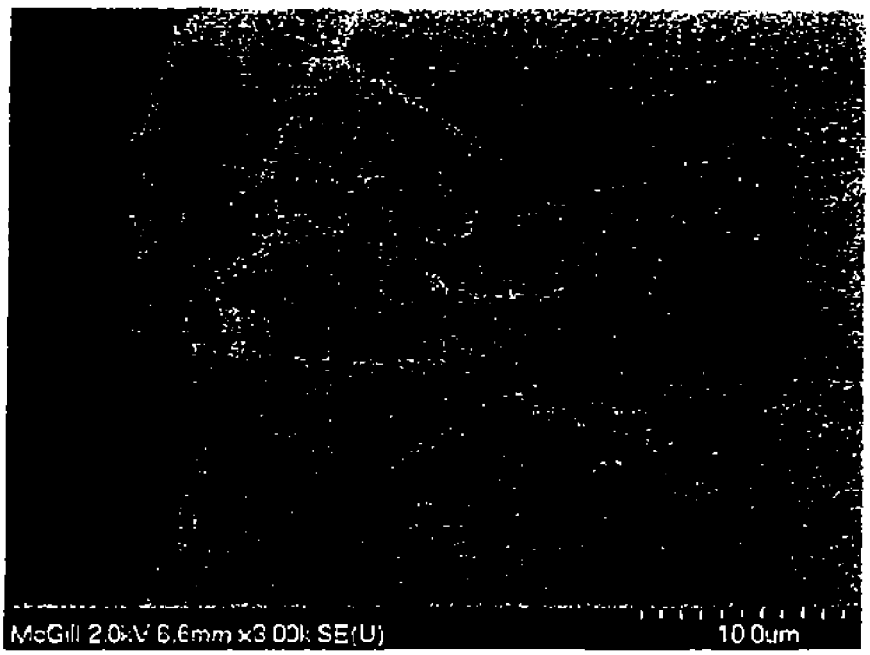
Figure 17B:
Figure 17C:
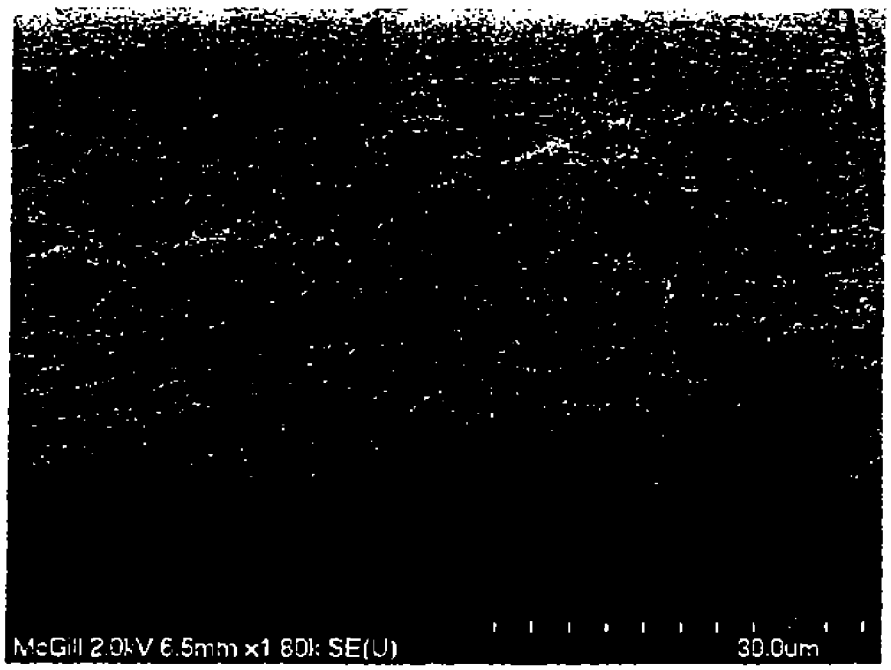
Figure 17D:
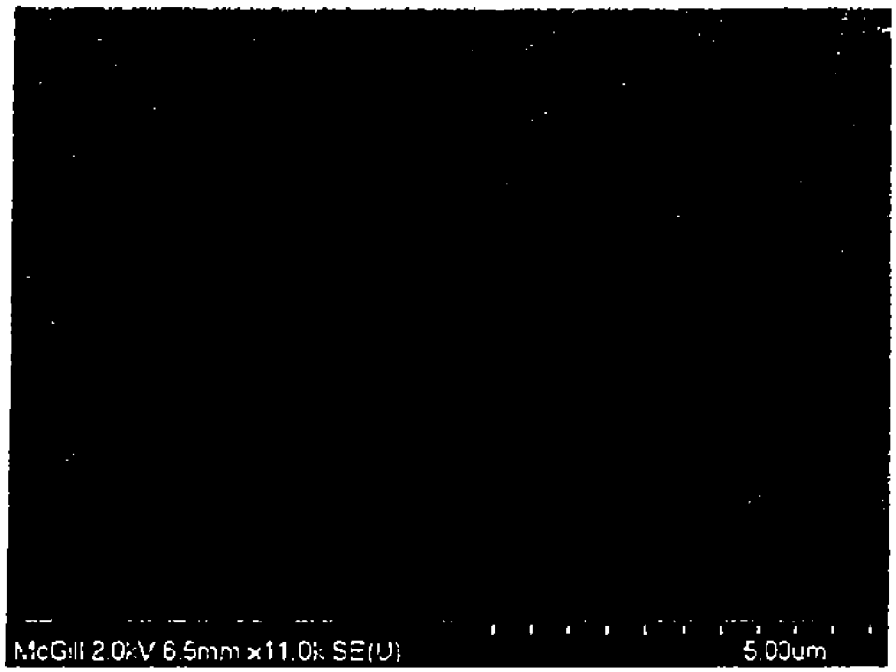

Equal volumes of saturated solutions of calcium chloride and sodium pyrophosphate in ethanol at room temperature were mixed in the presence of undissolved sodium pyrophosphate salt in a Petri dish. Water was then added. Round white masses formed that were visible with the naked eye. Under light microscopy the round white masses appeared brown and dendritically crystalline. SEM investigation of a broken particle (FIGS. 16A and 16B) showed that the crystalline patterning was limited to the surface layer (thickness about 100 nm) and the particle itself consisted of a core of nanofibers (FIGS. 17A-17D).

Example 14

This example describes another method for producing calcium pyrophosphate particles.

At room temperature, an initial mixture was made of equal volumes of a 300 mM aqueous calcium chloride solution (pH 7) and a 150 mM aqueous solution of tetrasodium pyrophosphate and sodium phosphate ($Na_3PO_4$) ($Na_3PO_4.12H_2O$ obtained from Fisher Scientific, Cat. No. S377-500) (pH 7) wherein the aqueous solution contained 80, 60, 50, 40, and 20% (mol) pyrophosphate ion ($P_2O_7^{4-}$) and 20, 40, 50, 60, and 80% (mol) orthophosphate ion (in successive experiments two orthophosphate ions replaced every pyrophosphate ion).

The results of these experiments were as follows:

Using an aqueous solution having 80% pyrophosphate ion:
    Spherical particle formation was retarded and crystals were not observed to form.

Using aqueous solutions having 40%, 50%, and 60% pyrophosphate ion:
    There was formation of a stable and very viscous gel. After about more than one month, all of the gel changed to crystallized precipitate.

Using an aqueous solution having 20% pyrophosphate ion:
    There was no formation of spherical particles. Only needle crystals formed.

Example 15

This example describes experiments conducted to test the effects of modifying viscosity of the solutions used to produce calcium pyrophosphate particles.

An initial mixture of equal volumes of a 300 mM aqueous calcium chloride solution (pH 7) and a 150 mM aqueous tetrasodium pyrophosphate solution (pH 7) was prepared. 5 mL of glycerine was added to 8 mL of the initial mixture. Fibrous calcium pyrophosphate particles formed. The addition of glycerine to the initial mixture of calcium chloride and tetrasodium pyrophosphate solution appeared to disperse the spherical particles and appeared to have no effect on particle size.

Another initial mixture was made by mixing 22.5 mL 300 mM aqueous calcium chloride solution (pH 7) and 22.5 mL 150 mM aqueous tetrasodium pyrophosphate solution (pH 7) with 41 mL of a solution containing 30 grams (g) sucrose in water. Very small spherical particles formed and grew over time. Within about one-half hour to one hour, the spherical particles stopped growing.

Viscosity was also increased by adding sucrose to each starting solution. In this experiment, an initial mixture was made of 60 mL of a 300 mM aqueous calcium chloride solution in which 24.21 grams (g) of sucrose was previously dissolved and 60 mL of a 150 mM aqueous tetrasodium pyrophosphate (pH 7) in which 26 g of sucrose was previously dissolved. Very small spherical particles formed and grew over time. Within about one-half hour to one hour, the spherical particles stopped growing.

Example 16

This example describes another method for production of calcium pyrophosphate particles.

Figure 18A:
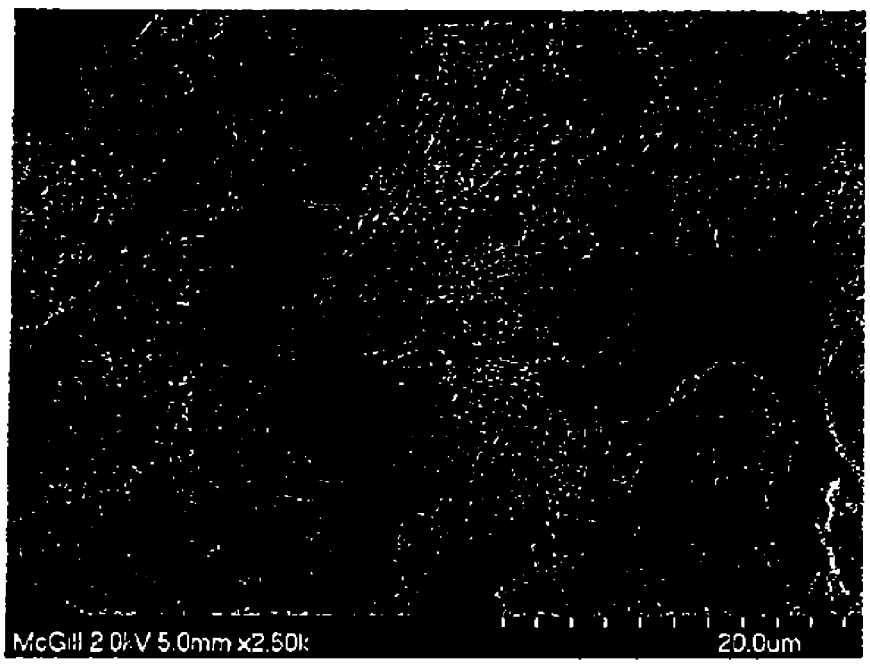
FIGS. 18A and 18B are photomicrographs of calcium pyrophosphate particles formed using an aqueous sodium chloride according to one embodiment of the present invention.
Figure 18B:
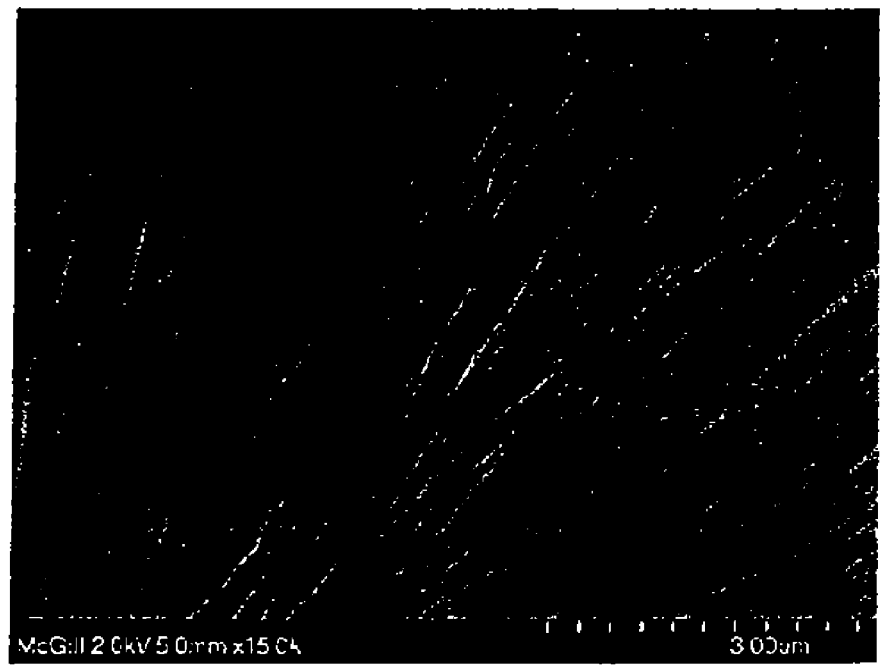

An initial mixture of equal volumes of a 300 mM aqueous calcium chloride solution and a 150 mM aqueous tetrasodium pyrophosphate solution was prepared. 5M aqueous sodium chloride (NaCl) was added to the initial mixture. The resulting particles had a distinct morphology with the particles made from stacks of nanoplates or fibers. FIGS. 18A and 18B are photomicrographs of the resulting particles.

Example 17

This example describes another method for production of calcium pyrophosphate particles.

20 mL of 150 mM aqueous tetrasodium pyrophosphate solution (pH 7) was dripped slowly over 20 minutes into 20 mL of 300 mM aqueous calcium chloride solution (pH 7). The pH of the resulting mixture was between 3.3 and 3.2. The first particles formed were smaller than particles formed, as described supra, by mixing equal volumes of a 300 millimolar (mM) aqueous calcium chloride solution (pH 7) and a 150 mM aqueous tetrasodium pyrophosphate ($Na_4P_2O_7$) solution (pH 7).

In another experiment, 20 mL of 300 mM aqueous calcium chloride solution (pH 7) was dripped slowly over 7 minutes into 20 mL of 150 mM aqueous tetrasodium pyrophosphate solution (pH 7). During the experiment, pH dropped from 6.7 (no mixture) to 5.07. An amorphous white product formed that transformed to fibrous particles after 25 minutes, during which time pH fell to bellow 4.

EQUIVALENTS

While this invention has been particularly shown and described with references to preferred embodiments thereof, it will be understood by those skilled in the art that various changes in form and details may be made therein without departing from the scope of the invention encompassed by the appended claims.

What is claimed is:

1. A composition comprising fibrous particles, the fibrous particles comprising:
   fibers, wherein the fibers comprise calcium and pyrophosphate, and
   a fatty acid, or a salt thereof.

2. A composition comprising fibrous particles, the fibrous particles comprising:
   fibers, wherein the fibers comprise calcium and pyrophosphate, and
   a pharmaceutically active ingredient.

3. A composition, comprising fibrous particles, the fibrous particles comprising:
   fibers, wherein the fibers comprise calcium and pyrophosphate, and
   an agent to prevent opsonisation.

4. The composition of claim 1, wherein the particles are microscale assemblies.

5. The composition of claim 2, wherein the particles are microscale assemblies.

6. The composition of claim 1, wherein the particles have a size of about 100 nm to about 100 μm.

7. The composition of claim 2, wherein the particles have a size of about 100 nm to about 100 μm.

8. The composition of claim 1, wherein the particles are porous.

9. The composition of claim 2, wherein the particles are porous.

10. The composition of claim 1, further comprising molecules selected from deoxyribonucleic acid (DNA), ribonucleic acid (RNA), peptides, proteins, carbohydrates, and polycarbohydrates.

11. The composition of claim 2, further comprising molecules selected from deoxyribonucleic acid (DNA), ribonucleic acid (RNA), peptides, proteins, carbohydrates, and polycarbohydrates.

12. The composition of claim 3, further comprising molecules selected from deoxyribonucleic acid (DNA), ribonucleic acid (RNA), peptides, proteins, carbohydrates, and polycarbohydrates.

13. The composition of claim 3, wherein the agent is polyethylene glycol (PEG).

14. The composition of claim 1, wherein the composition is in the form of a tablet.

15. The composition of claim 2, wherein the composition is in the form of a tablet.

16. The composition of claim 1, wherein the fibers are amorphous, nanocrystalline or both.

17. The composition of claim 2, wherein the fibers are amorphous, nanocrystalline or both.

18. The composition of claim 2, wherein the fibers further comprise magnesium.

19. The composition of claim 2, wherein the fibers further comprise an alkali metal, a transition metal, or an ion thereof.

20. The composition of claim 2, wherein the particles are spherical.

21. The composition of claim 2, wherein the particles are disk-shaped.

22. The composition of claim 2, wherein the particles are stabilized.

* * * * *